United States Patent
Agrewala et al.

(10) Patent No.: US 9,340,622 B2
(45) Date of Patent: May 17, 2016

(54) SYNTHETIC IMMUNOGEN USEFUL FOR GENERATING LONG LASTING IMMUNITY AND PROTECTION AGAINST PATHOGENS

(75) Inventors: Javed N. Agrewala, Chandigarh (IN); Uthaman Gowthaman, Chandigarh (IN); David Jackson, Parkville (AU); Weiguang Zeng, Parkville (AU)

(73) Assignees: Council of Scientific & Industrial Research, New Delhi (IN); University of Melbourne, Victoria (AU)

( * ) Notice: Subject to any disclaimer, the term of this patent is extended or adjusted under 35 U.S.C. 154(b) by 0 days.

(21) Appl. No.: 13/822,881

(22) PCT Filed: Sep. 14, 2011

(86) PCT No.: PCT/IN2011/000630
§ 371 (c)(1),
(2), (4) Date: Mar. 13, 2013

(87) PCT Pub. No.: WO2012/035558
PCT Pub. Date: Mar. 22, 2012

(65) Prior Publication Data
US 2013/0183377 A1    Jul. 18, 2013

(30) Foreign Application Priority Data
Sep. 14, 2010    (IN) ............... 2172/DEL/2010

(51) Int. Cl.
| A61K 39/04 | (2006.01) |
| A61K 39/02 | (2006.01) |
| A61K 39/00 | (2006.01) |
| C07K 19/00 | (2006.01) |

(52) U.S. Cl.
CPC ............ *C07K 19/00* (2013.01); *A61K 39/04* (2013.01); *A61K 2039/55516* (2013.01); *A61K 2039/6018* (2013.01)

(58) Field of Classification Search
CPC ........ A61K 39/00; A61K 39/02; A61K 39/04
USPC ............ 424/9.1, 9.2, 184.1, 185.1, 234.1, 424/248.1; 530/300, 350
See application file for complete search history.

(56) References Cited

U.S. PATENT DOCUMENTS
2002/0131975 A1    9/2002    Horwitz et al.

FOREIGN PATENT DOCUMENTS
| GB | 2239246 A | 6/1991 | |
| WO | WO2004/014957 A1 * | 2/2004 | ............ C07K 19/00 |
| WO | WO-2004014957 A1 | 2/2004 | |

OTHER PUBLICATIONS

Eidel et al., "Notification of Transmittal of the International Search Report and the Written Opinion of the International Searching Authority, or the Declaration", Patent Cooperation Treaty, Apr. 12, 2012, 29 pages, PCT/IN2011/000630, European Patent Office, Rijswijk, Netherlands.

Mustafa et al., "Identification and HLA Restriction of Naturally Derived Th1-Cell Epitopes from the Secreted *Mycobacterium tuberculosis* Antigen 85B Recognized by Antigen-Specific Human CD4 T-Cells Lines", Infection and Immunity, vol. 68, 2000, pp. 3933-3940.

Zeng et al., "Highly Immunogenic and Totally Synthetic Lipopeptides as Self-Adjuvanting Immunocontraceptive Vaccines", Journal of Immunology, vol. 169, 2002, pp. 4905-4912.

Written Opinion of the International Searching Authority for corresponding International application Serial No. PCT/IN2011/000630, Mar. 19, 2013, 8 pages.

* cited by examiner

*Primary Examiner* — Rodney P Swartz
(74) *Attorney, Agent, or Firm* — Locke Lord LLP; Barry Kramer; Gabriel J. McCool

(57) ABSTRACT

The present invention relates to a synthetic immunogen represented by the general formula 1, useful for generating long lasting protective immunity against various intracellular pathogens which are the causative agents of tuberculosis, leishmaniasis, AIDS, trypanosomiasis, malaria and also allergy, cancer and a process for the preparation thereof. The developed immunogen is able to circumvent HLA restriction in humans and livestock. The invention further relates to a vaccine comprising the said immunogen for generating enduring protective immunity against various diseases. The said vaccine is targeted against intracellular pathogens, more particularly the pathogen *M. tuberculosis* in this case. In the present invention, promiscuous peptides of *M. tuberculosis* are conjugated to TLR ligands especially; Pam2Cys to target them mainly to dendritic cells and therefore elicit long-lasting protective immunity.

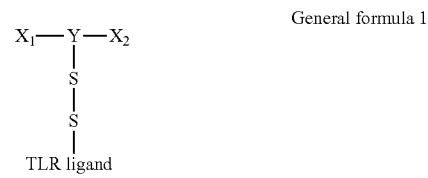

Figure 2:
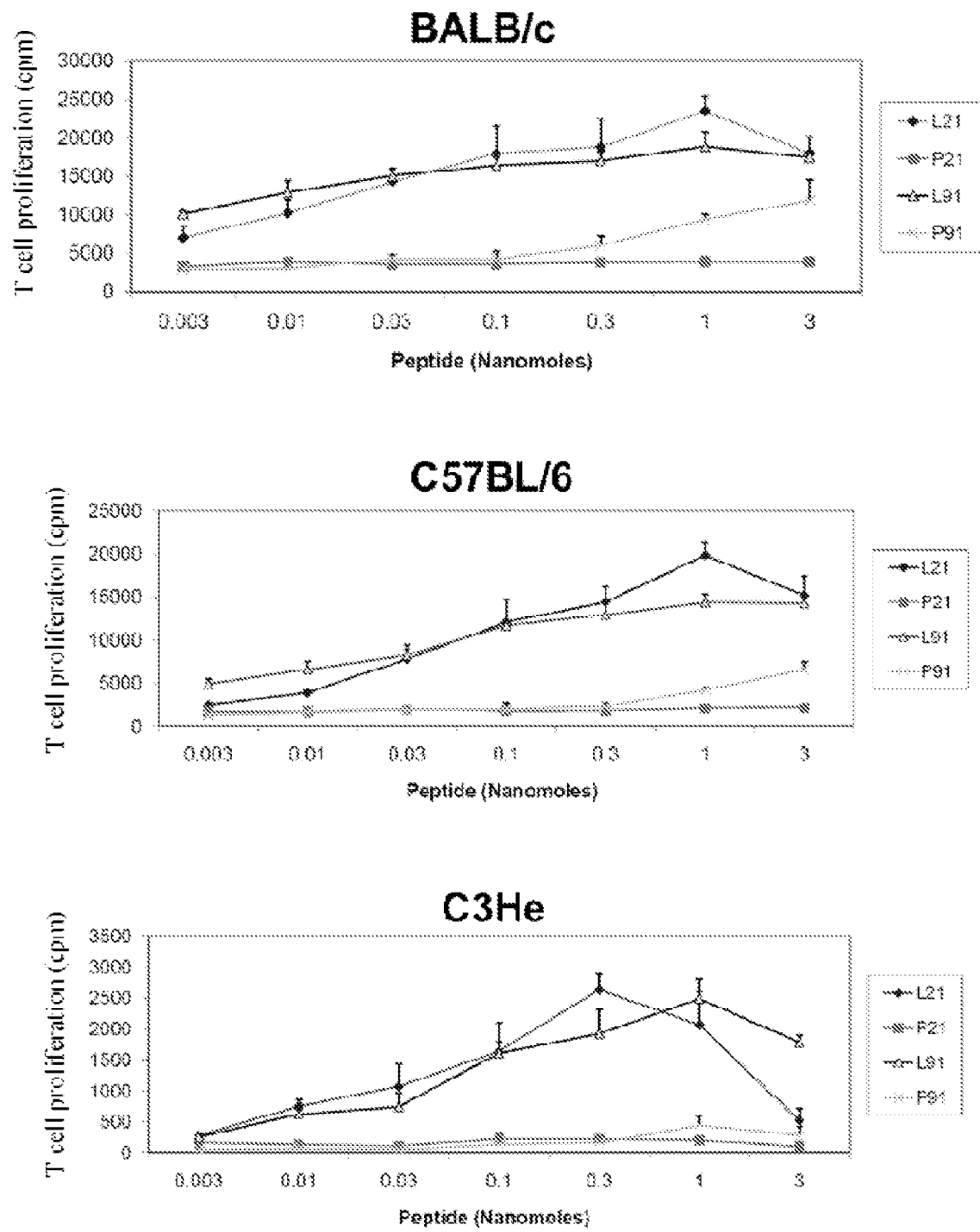

General formula 1 wherein, $X_1$=a promiscuous CD4 T helper epitope selected from SEQ ID No. 1 to 98 OR nil;
$X_2$=a promiscuous CD8 T cytotoxic epitope selected from SEQ ID No. 99 to 103 OR nil;
when X1=nil; X2=SEQ ID No. 99 to 103 and when X2=nil; X1=SEQ ID No. 1 to 98;
Y=Lysine; and
S=Serine.

14 Claims, 13 Drawing Sheets

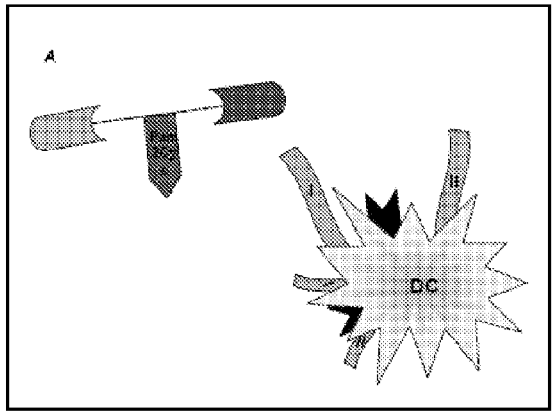
Fig. 1A
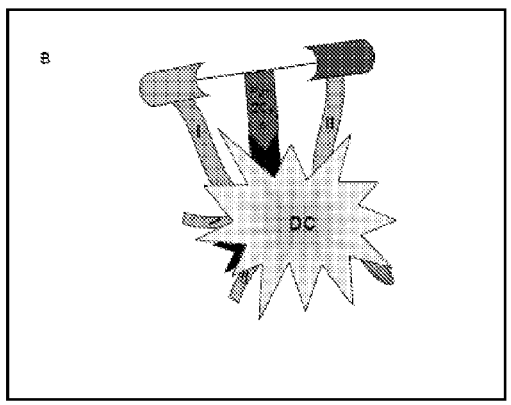
Fig. 1B
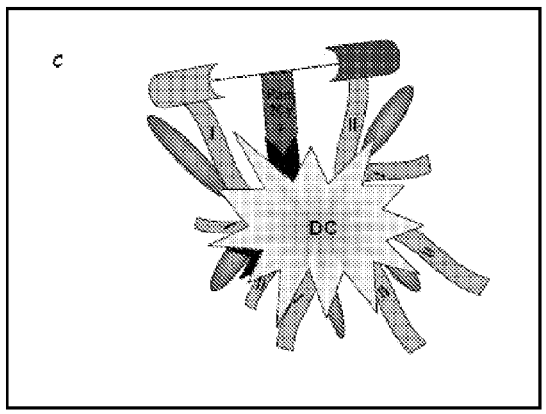
Fig. 1C
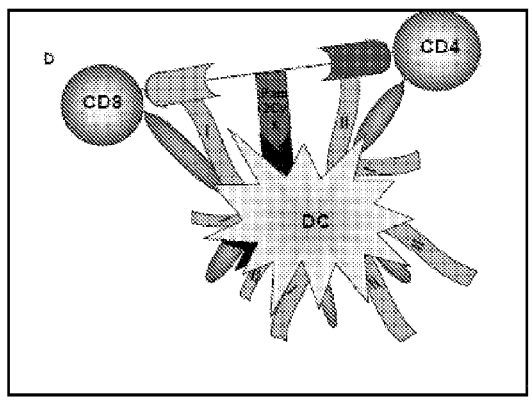
Fig. 1D
FIG. 1

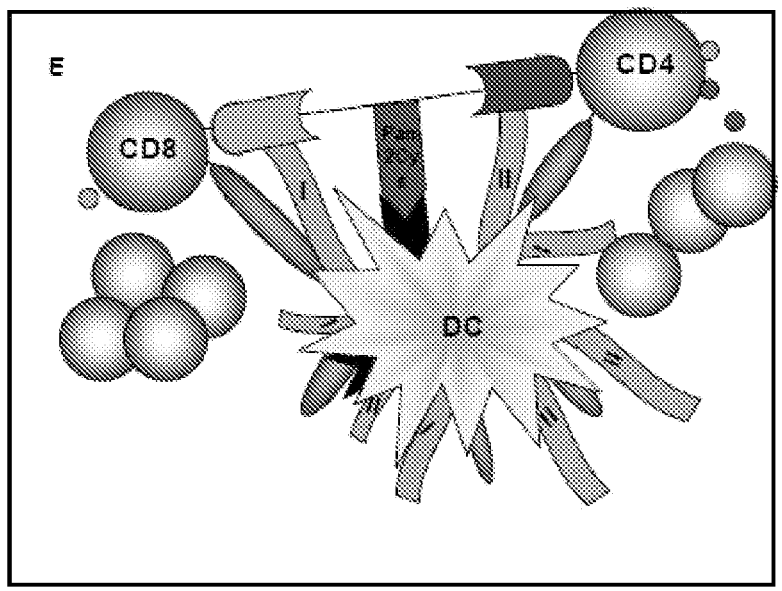
Fig. 1E
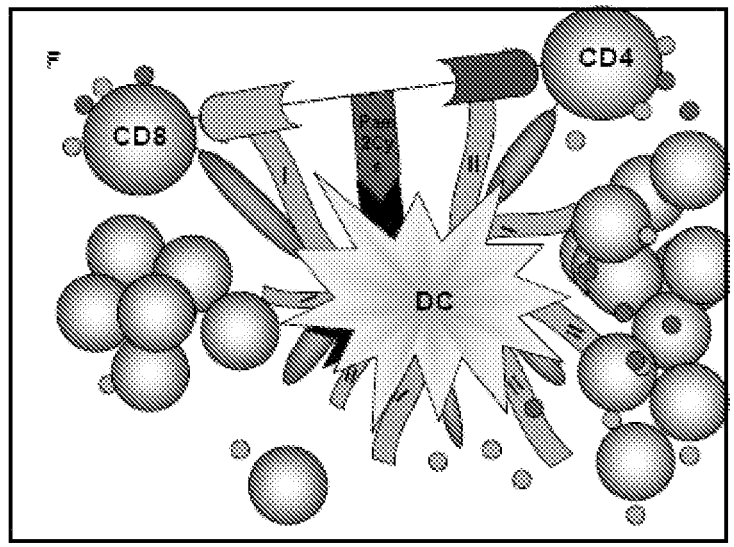
Fig. 1F
FIG. 1 (cont'd)

GM= Geometric Mean of Fluorescence

SYNTHETIC IMMUNOGEN USEFUL FOR GENERATING LONG LASTING IMMUNITY AND PROTECTION AGAINST PATHOGENS

FIELD OF INVENTION

The present invention relates to a synthetic immunogen useful for generating long lasting immunity and protection against pathogens and a process for the preparation thereof. The developed immunogen is able to circumvent HLA restriction in humans. The invention further relates to a vaccine comprising the said immunogen for generating long lasting immunity and protection against various diseases. The said vaccine is targeted against intracellular pathogens, more particularly the pathogen *Mycobacterium tuberculosis* (*M. tuberculosis*), in this case. The pathogen *M. tuberculosis* the subject matter of this invention is the causative agent of tuberculosis. The vaccine is also useful against the intracellular pathogens, which are causative agents of brucellosis, leishmaniasis, listeriosis, leprosy, malaria, typhoid, trypanosomiasis, streptococcus, acquired immunodeficiency syndrome (AIDS), and also for diseases like cancer, allergy, autoimmunity, etc. In the present invention, promiscuous epitopes of *M. tuberculosis* are conjugated to Toll-like receptor (TLR) ligands to target them to antigen presenting cells (APCs), in particular to dendritic cells (DCs) and therefore elicit enduring protective immunity.

BACKGROUND OF INVENTION & DESCRIPTION OF PRIOR ART

According to the World Health Organization (WHO) report (2000), 100 million newborns and children received BCG in 1992 through WHO/UNICEF program. Even though majority of the global population is vaccinated with BCG, tuberculosis continues to kill some 3 million people a year. Further, about one-third of the world population remains latently infected with *M. tuberculosis*. Hence, the only available vaccine BCG is both unpredictable and highly variable. Doubtful efficacy of BCG vaccination has put the scientific community to challenge to urgently develop effective means of vaccination against *M. tuberculosis*.

Unfortunately, the global problem of tuberculosis is compounded by the additional problems of AIDS and emergence of Multi Drug Resistant (MDR) strains of *M. tuberculosis*. Moreover, a new question has arisen regarding the safety of BCG in HIV-infected individuals. A small number of cases of disseminated BCG-osis have been reported among children who received BCG vaccine and were subsequently found to be HIV seropositive (Von Reyn, et. al. *Lancet* 1987:ii:669-672; Braun, et. al., *Pediatr. Infect. Dis. J.* 1992:11:220-227; Weltman, et. al., *AIDS* 7:1993:149). WHO currently recommends discontinuing the use of BCG vaccine in children showing overt signs of immunodeficiency (World Health Organization. Tuberculosis fact sheet number 104, August 2002).

BCG has been extensively utilized globally and in spite of its intrepid use, tuberculosis has still become the fastest spreading disease not only in developing countries but also in the industrialized world. Its doubtful efficacy in controlled trials has increased the concern about its use as a vaccine (Bloom, B. R. et. al., Annu. Rev. Immunol. 10:1992:453). Furthermore, the extensive clinical trials done in Chenglepet, India showed similar extent of protection in BCG-vaccinated and unvaccinated individuals, indicating that it induced zero protection (Narayanan *Indian J Med Res.* 2006, 123 (2): 119-124). Thus it is obvious that BCG vaccination does not prevent transmission.

Another insight for BCG failure is provided by the intracellular location of the mycobacterium. Electron microscopic findings indicate that BCG remains essentially within the phagolysosomes after in vitro infection of macrophages, whereas virulent *M. tuberculosis* (strain H37Rv) can escape from the phagolysosome and enter the cytoplasm (McDonough, et. al., *Infect. Immun.* 61:1993:2763). This may be relevant insofar as it is the antigens in the endosomal compartment of antigen-presenting cells that are presented in conjunction with MHC class II determinants to $CD4^+$ T helper cells, whereas cytoplasmic antigens are presented in association with the Major Histocompatibility Complex (MHC) class I determinants to $CD8^+$ Cytotoxic T cells (CTL). This explains why *M. tuberculosis* is more dependent for its elimination on MHC class I-restricted CTL than BCG and suggests that BCG may not be very effective in eliciting MHC class I-restricted CTL (Stover, et. al., *Nature* 351:1991:456). In this context, Rich, 1951, Kaufman et al 2008, commented that recovery from infection with *M. tuberculosis* provided stronger protection against future tuberculosis than could BCG. Hence, the effective resistance to *M. tuberculosis* infection will require participation both of specific $CD8^+$ CTL to lyse macrophages or parenchymal cells unable to restrict their infection and of specific $CD4^+$ T cells able to produce IL-2, IFN-$\gamma$, TNF-$\alpha$, and other lymphokines involved in macrophage activation.

Recent series of studies have suggested that *M. tuberculosis*/environmental mycobacteria actively inhibit bacterial antigen processing and presentation by MHC-I and MHC-II pathways, thus slowing the emergence of protective adaptive immunity (Wolf A J, Linas B, Trevejo-Nuñez G J, Kincaid E, Tamura T, Takatsu K, Ernst J D. *Mycobacterium tuberculosis* infects dendritic cells with high frequency and impairs their function in vivo. J Immunol. 2007, 179(4):2509-19). Furthermore, *M. tuberculosis* also impairs in vivo antigen processing of dendritic cells (Wolf A J, Linas B, Trevejo-Nuñez G J, Kincaid E, Tamura T, Takatsu K, Ernst J D. *Mycobacterium tuberculosis* infects dendritic cells with high frequency and impairs their function in vivo. J Immunol. 2007, 179(4):2509-19). Hence failure of BCG in endemic areas like India can be suggested to be due to the extensive mycobacterial load in the environment. Consequently, antigen processing pathways might be seriously compromised. To overcome these problems, a suitable approach in TB-endemic areas may be to devise a vaccine that bye pass antigen processing. Hence peptides can be suitable alternative since they do not require extensive antigen processing.

Peptides can be potentially used as vaccines. They bypass antigen processing because they can directly bind to MHC class I and II molecules; hence can be presented to both CD4 and CD8 T cells. Therefore the environmental mycobacterial load will not affect their efficacy. Unfortunately, conventional peptide vaccines have been plagued by two problems. Firstly, peptides are poorly immunogenic. They have to be administered with powerful adjuvants to elicit an immune response. The number of adjuvants available for humans are not only extremely limited but are also very expensive. Therefore such a strategy is economically not viable for mass vaccination, especially in developing countries, where tuberculosis incidence is maximal. Secondly, most of the antigenic peptides derived from mycobacterial antigen's binding is restricted to just one or two Human Leukocyte Antigen (HLA) alleles. HLA is the most polymorphic gene system in the entire human genome. Therefore it is difficult for the peptides to elicit an immune response in a genetically diverse human population, which is thoroughly polymorphic. These reasons have mired progress in peptide vaccinology. But if these problems are circumvented, peptide vaccine can be extremely effective than any other potential candidates; particularly in a situation where antigen processing is stalled by environmental agents. Further, promiscuous peptides, which can bind to many HLA alleles, can solve the problem of HLA restriction. Therefore identification of promiscuous peptides from antigens of *M. tuberculosis*, especially secretory antigens, would be of great importance in developing a vaccine. Promiscuous T cell epitopes are peptides that bind to more than one HLA allele and hence may elicit a T cell response overcoming MHC restrictions. They can be identified by conventional biochemical in vitro HLA binding assays, immunologic assays such as T cell proliferation, and activation or effector response such as secretion of cytokines (Agrewala J N, Deacock S, Jurcevic S, Wilkinson R. Peptide recognition by T-cell clones of an HLA-DRB1*1501/*0901 heterozygous donor is promiscuous only between parental alleles. Peptide recognition by T-cell clones of an HLA-DRB1*1501/*0901 heterozygous donor is promiscuous only between parental alleles. Hum Immunol. 1997 June; 55(1):34-8; Agrewala J N, Wilkinson R J. Differential regulation of Th1 and Th2 cells by p91-110 and p21-40 peptides of the 16-kD alpha-crystallin antigen of *Mycobacterium tuberculosis*. Differential regulation of Th1 and Th2 cells by p91-110 and p21-40 peptides of the 16-kD alpha-crystallin antigen of *Mycobacterium tuberculosis*. Clin Exp Immunol. 1998 December; 114(3):392-7; Agrewala J N, Wilkinson R J. Influence of HLA-DR on the phenotype of CD4+T lymphocytes specific for an epitope of the 16-kDa alpha-crystallin antigen of *Mycobacterium tuberculosis*. Influence of HLA-DR on the phenotype of CD4+T lymphocytes specific for an epitope of the 16-kDa alpha-crystallin antigen of *Mycobacterium tuberculosis*. Eur J Immunol. 1999 June; 29(6):1753-61). They may also be selected based on bioinformatic analysis using T cell epitope prediction programs.

The pre-requisite for the effective priming of the adaptive immune system is the maturation of APCs, whose function is to engulf the pathogens, process and present it to T cells. Antigen presenting cells possess Pattern Recognition Receptors (PRRs) which recognize the conserved motifs known as Pathogen Associated Molecular Patterns (PAMPs) of the pathogens. Triggering of PRRs by PAMPs acts as a "danger signal" (Medzhitov R, Janeway C A Jr. Innate immunity: the virtues of a nonclonal system of recognition. Cell. 1997 Oct. 31; 91(3):295-8), which results in maturation of APCs and culminates in mounting an adaptive immune response against that pathogen. Toll-Like Receptors are one such critical PRRs which link the innate and adaptive arms of immunity. Adjuvants functions by binding to TLRs and thereby delivering signals necessary for the activation of APCs. Recently, it has been demonstrated very elegantly that there is robust increase in the immune response if TLR triggering moiety and the antigen are physically associated (Blander J M, Medzhitov R Toll-dependent selection of microbial antigens for presentation by dendritic cells. Nature. 2006, 440(7085):808-12).

Expression of costimulatory molecules, enhanced antigen presentation and production of cytokines and chemokines is also upregulated when APCs are engaged with TLRs. In essence, TLRs are a family of transmembrane receptors by which APCs recognize the conserved PAMPs that distinguish the infectious agents from self. Over the past few years, the macromolecules recognized by TLRs have been identified. Agonists for TLRs include the inflammatory mediators triacyl lipopeptides (TLR1), lipoteichoic acid (TLR2), dsRNA (TLR3), lipopolysaccharide (TLR4), flagellin (TLR5), diacyl lipopeptides (TLR6), imidazoquinolines (TLR7, TLR8) and CpG oligonucleotides (TLR9) (Akira S, Sato S. Toll-like receptors and their signaling mechanisms. Scand J Infect Dis. 2003; 35(9):555-62). Toll like receptors constitute an essential part of the innate immune system but they have also been equally important in adaptive immune system. Antigen presentation without this danger signal leads to anergy or tolerance.

Hence, an analysis of the hitherto reported literature reveals that free peptides may not elicit an optimum immune response. Since TLR triggering is essential for activation of the APCs, physically coupling (covalent or encapsulated form) promiscuous peptides/epitopes to TLR ligands to trigger effective immune response may be an exceptional proposition. Most of the TLR ligands are lipid moieties but TLR 3, 7 and 9 are triggered by nucleic acids. Triggering of TLRs especially, TLRs 2, 4 and 9 results in Th1 responses. Hence, it is specially proposed that these peptide-TLR ligands for 2 or 4 or 9 would be very effective in protecting against *M. tuberculosis*.

Despite several potential advantages none of the totally synthetic peptide epitope-based vaccines are yet licensed/available for human or animal use. The poor immunogenicity of peptides in the absence of co-administered adjuvants and the paucity of adjuvant systems suitable for human use has limited the development of viable epitope-based vaccines.

Accordingly, it may be summarized that non-living vaccines fails to impart protection against tuberculosis due to the use of inadequate adjuvants. The currently-used adjuvants for human vaccines (based on aluminum salts) are only effective in vaccines that require a humoral response since they bias the immune response towards the Th2 pole, which can only help in protecting against extra-cellular infections. The available adjuvants have limited use due to their very high cost. Thus, an effective way to overcome this predicament is to incorporate lipid groups into the promiscuous-peptides/subunit vaccines which will then have self-adjuvanting properties.

OBJECTS OF THE INVENTION

The main object of the present invention is thus to develop an immunogen that obviates the drawbacks as detailed above.

Another object of the present invention is to provide an immunogen that is useful for generating long lasting protective immunity against intracellular pathogens, which are the causative agents of tuberculosis, brucellosis, leishmaniasis, listeriosis, leprosy, malaria, typhoid, trypanosomiasis, streptococcus, AIDS, and also diseases like cancer, allergy and autoimmunity.

Yet another object of the present invention is to provide an immunogen which is able to circumvent HLA restriction in humans.

Yet another object of the present invention is to provide an immunogen comprising of promiscuous peptides/epitopes from *M. tuberculosis* proteome coupled to TLR ligands.

Still another object of the present invention is to provide lipidated promiscuous peptides/epitopes from *M. tuberculosis* that enhances enduring CD4$^+$ and CD8$^+$ T cell memory and impart protective immunity against tuberculosis.

Another object of the present invention is to provide lipidated promiscuous peptides/epitopes from *M. tuberculosis* that can mainly induce the secretion of cytokines interferon-gamma (IFN-γ) and interleukin-12 (IL-12).

Another object of the present invention is to provide lipidated promiscuous peptides/epitopes from *M. tuberculosis* that can reduce the bacterial burden from pulmonary and extra-pulmonary regions of the body.

Another object of the present invention is to provide a pharmaceutical composition comprising the said immunogen.

A further object of the present invention is to provide a vaccine based on surface coating or encapsulation of the promiscuous peptides/epitopes of *M. tuberculosis* to nanoparticles.

SUMMARY OF THE INVENTION

The present invention relates to a process for eliciting an effective immune response against intracellular pathogens, especially *M. tuberculosis*. This is achieved by developing a synthetic immunogen comprising of promiscuous peptides/epitopes from *M. tuberculosis* linked to a TLR ligand. The said immunogen can either be in a free form or encapsulated in nanoparticles and/or liposomes so that it can effectively elicit a robust and long-lasting protective immune response. The invention further relates to a pharmaceutical composition in the form of a vaccine based on surface coating or encapsulation of the promiscuous peptides/epitopes of *M. tuberculosis* to nanoparticles for imparting long-lasting immunity against *M. tuberculosis*. The developed immunogen may also be covalently coupled to/entrapped in mannosylated liposomes or liposomes tagged with anti-DEC-205 antibody for evoking the desired immune response.

The developed synthetic immunogen comprises of promiscuous peptides/epitopes from *M. tuberculosis* proteome represented by SEQ ID Nos. 1 to 103 (Table 1). The promiscuous peptides are identified based on binding to HLA class I (HLA-A, B, C) and HLA class II (HLA-DR, DP, DQ) molecules, T cell proliferation, cytokines (IL-2, IL-4, IL-12, IFN-γ) secretion and in silico methods.

The identified MHC I and MHC II binding promiscuous peptides are either covalently coupled to TLR ligands selected from TLR1, TLR2, TLR3, TLR4, TLR5, TLR6, TLR7, TLR8, TLR9, TLR10, TLR11, TLR12, TLR13 (such as diacyl lipopeptides, triacyl lipopeptides, lipoarabinomanan, lipoteichoic acid, dsRNA, lipopolysaccharide, flagellin, diacyl lipopeptides, imidazoquinolines and CpG oligonucleotides, etc) that are amenable to such coupling through a serine and/or lysine linker. Further, the peptides may be encapsulated in synthetic nanoparticles or liposomes, so that they are effectively presented to CD4 and CD8 T cells by APCs, especially the dendritic cells (FIG. 1).

Accordingly, the present invention provides a synthetic immunogen useful for generating long-lasting immunity against *M. tuberculosis*, wherein the said immunogen is represented by the general formula 1:

General formula 1

$$X_1 - Y - X_2$$
$$|$$
$$S$$
$$|$$
$$S$$
$$|$$
$$\text{TLR ligand}$$

wherein, $X_1$=a promiscuous CD4 T helper epitope selected from SEQ ID No. 1 to 98 OR nil; $X_2$=a promiscuous CD8 T cytotoxic epitope selected from SEQ ID No. 99 to 103 OR nil; when X1=nil; X2=SEQ ID No. 99 to 103 and when X2=nil; X1=SEQ ID No. 1 to 98; Y=Lysine; and S=Serine.

In an embodiment, the present invention provides a synthetic vaccine comprising of promiscuous peptides (capable of binding to several MHC I and MHC II molecules) selected from *M. tuberculosis* linked to TLR2 ligand Pam2Cys and targeted to dendritic cells for eliciting both CD4 and CD8 T cell response.

In another embodiment, the present invention provides a synthetic vaccine comprising of promiscuous peptides of *M. tuberculosis* linked to TLR2 ligand Pam3Cys.

In yet another embodiment, the present invention a synthetic vaccine comprising of promiscuous peptides of *M. tuberculosis* linked to TLR2, ligand lipopeptide MALP-2.

In still another embodiment, the present invention a synthetic vaccine comprising of promiscuous peptides of *M. tuberculosis* linked to TLR4 ligand lipopolysaccharide (LPS).

In yet another embodiment, the present invention a vaccine comprising of promiscuous peptides of *M. tuberculosis* linked to TLR9 ligand CpG oligonucleotides (CpG ODN).

In still another embodiment, the present invention provides a vaccine based on surface coating or encapsulation of promiscuous peptides of *M. tuberculosis* to nanoparticles.

In still another embodiment, the present invention provides a vaccine based on surface coating or encapsulation of promiscuous peptides of *M. tuberculosis* to liposomes.

In yet another embodiment, the present invention provides a vaccine by mixing promiscuous CD4 and CD8 epitopes of *M. tuberculosis* with TLR agonists.

In another embodiment, the present invention provides a process for the preparation of the vaccine by mixing promiscuous CD4 and CD8 epitopes of *M. tuberculosis* with nanoparticles.

In another embodiment, the present invention provides a process for the preparation of the vaccine by mixing promiscuous CD4 and CD8 epitopes of *M. tuberculosis* with liposomes.

In another embodiment, the present invention provides a process for preparation of a vaccine, wherein the main rationale for encapsulation is for those situations where covalent coupling is not very amenable as in case of nucleic acids (ligands for TLRs 3, 7, 9) and when the TLR ligands are predominantly intracellular. However, the same strategy can be applied to TLRs 2, 4 and 5 as well because though they are predominantly expressed on the surface, they are also expressed in the endosomal compartments.

In another embodiment, the present invention provides an immunogen represented by the formula:

$$X_1 - Y$$
$$|$$
$$S$$
$$|$$
$$S$$
$$|$$
$$\text{TLR ligand}$$

wherein, $X_1$=a promiscuous CD4 T helper epitope selected from SEQ ID No. 1 to 98; and Y=Lysine; and S=Serine.

In yet another embodiment, the present invention provides an immunogen represented by the formula:

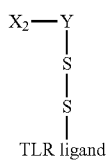

wherein, $X_2$=a promiscuous CD8 T cytotoxic epitope selected from SEQ ID No. 99 to 103; and Y=Lysine; and S=Serine.

In still another embodiment, the present invention provides an immunogen represented by the formula:

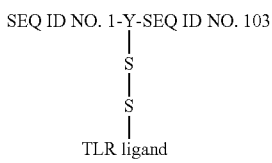

wherein, Y=Lysine and S=Serine.

In yet another embodiment, the present invention provides an immunogen wherein the promiscuous epitopes represented by SEQ ID No. 1 to 103 are from *Mycobacterium tuberculosis*.

In still another embodiment, the present invention provides an immunogen wherein the TLR ligand is selected from the group consisting of TLR1, TLR2, TLR3, TLR4, TLR5, TLR6, TLR7, TLR8, TLR9, TLR10, TLR11, TLR12 and TLR13 ligands.

In yet another embodiment, the present invention provides an immunogen wherein the TLR ligand is selected from the group consisting of diacyl lipopeptides, triacyl lipopeptides, lipoarabinomanan and lipopolysacharides.

In still another embodiment, the present invention provides an immunogen wherein the TLR ligand is S-[2,3-bis(palmitoyloxy)propyl]cysteine (Pam2Cys).

In yet another embodiment, the present invention provides an immunogen wherein the promiscuous epitopes from *M. tuberculosis* are identified based on binding to HLA class I (HLA-A, B, C) and HLA class II (HLA-DR, DP, DQ) molecules.

In still another embodiment, the present invention provides an immunogen wherein the promiscuous epitopes from *M. tuberculosis* are identified based on T cell proliferation and secretion of IFN-γ, IL-2, IL-4 and IL-12.

In yet another embodiment, the present invention provides an immunogen wherein the promiscuous epitopes from *M. tuberculosis* enhances MHC/HLA expression.

In still another embodiment, the present invention provides an immunogen wherein the promiscuous epitopes from *M. tuberculosis* enhances the expression of co-stimulatory molecules selected from CD80, CD86 and CD40.

In yet another embodiment, the present invention provides an immunogen wherein the promiscuous epitopes enhance the proliferation of $CD4^+$ and $CD8^+$ T cells and up regulates the expression of CD69 and CD44.

In still another embodiment, the present invention provides an immunogen wherein the promiscuous epitopes from *M. tuberculosis* modulates the secretion of cytokines IL-2, IL-4, IL-5, IL-6, IL-10, IL-12, IFN-γ and TNF-α.

In yet another embodiment, the present invention provides an immunogen wherein the promiscuous epitopes enhance $CD4^+$ and $CD8^+$ T cell memory, including both central and effector T cell memory.

In still another embodiment, the present invention provides an immunogen wherein the promiscuous epitopes modulates the expression of CD44, CD62L and CD127 on memory $CD4^+$ and $CD8^+$ T cells.

In still another embodiment, the present invention provides an immunogen wherein the promiscuous epitopes boosts pulmonary and extra-pulmonary immunity against *M. tuberculosis*.

In yet another embodiment, the present invention provides an immunogen wherein the promiscuous epitopes down regulate the expression of immune suppressive molecule like PD-1.

In still another embodiment, the present invention provides an immunogen wherein the promiscuous epitopes inhibit the generation of regulatory T cells.

In yet another embodiment, the present invention provides an immunogen wherein the promiscuous epitopes can induce proliferation of human lymphocytes from healthy and tuberculosis patients by inducing the secretion of IFN-γ.

In still another embodiment, the present invention provides an immunogen wherein it exploits TLR ligands as adjuvants and hence extra adjuvants are not required.

In yet another embodiment, the present invention provides an immunogen wherein it is targeted to antigen presenting cells like dendritic cells, macrophage and B cells.

In still another embodiment, the present invention provides an immunogen wherein it is coated to/encapsulated in nanoparticles.

In yet another embodiment, the present invention provides an immunogen wherein it is covalently coupled to/entrapped in mannosylated liposomes or liposomes tagged with anti-DEC-205 antibody.

In a further embodiment, the present invention provides a pharmaceutical injectable composition comprising the said immunogen optionally along with a pharmaceutically acceptable carrier, diluent or excipient.

In still further embodiment, the present invention provides a method of inducing an immune response against *M. tuberculosis* in a subject, comprising administering to the subject a therapeutically effective amount of the said immunogen optionally along with a pharmaceutically acceptable carrier, diluent or excipient.

BRIEF DESCRIPTION OF THE ACCOMPANYING DRAWINGS

FIG. 1. Mechanism of action of the immunogen. (A) As soon as the immunogen is administered, it seeks DCs due to their high expression of TLR2 ligands and MHC molecules. (B) due to high affinity for MHC and TLR2, the construct containing TLR2 ligand (Pam2cys), CD8 and CD4 epitopes binds to TLR2 and MHC molecules on DCs. (C) This activates DCs and makes them upregulate co-stimulatory and MHC molecules. (D) When peptides bind MHC-I and MHC-II, CD8 and CD4 T cells recognize their respective peptides presented in context with MHC-I and MHC-II molecules on activated DCs. (E) This activates antigen specific T cells. (F) This results in clonal expansion of CD4 T-helper cells and CD8 cytotoxic T cells and secretion of cytokines and results in promoting amplification of the immune response.

FIG. 2. Lipidated Promiscuous Peptides [developed immunogen] works permissively in different laboratory strains of mice. Genetically distinct strains of mice (BALB/c, C57BL/6, C3He) were used to test the ability of the developed immunogens to trigger T cell proliferation. Splenocytes from antigen exposed mice were stimulated with lipidated peptides [immunogen] and free peptides. T cell proliferation was measured using incorporation of $^3$H-thymidine after 48 hrs of in vitro challenge. Abbreviations used in the drawings: p21: free peptide SEQ ID No. 2, p91: free peptide SEQ ID No. 1, L21: lipidated peptide SEQ ID No. 2, L91: lipidated peptide SEQ ID No. 1.

Figure 3:
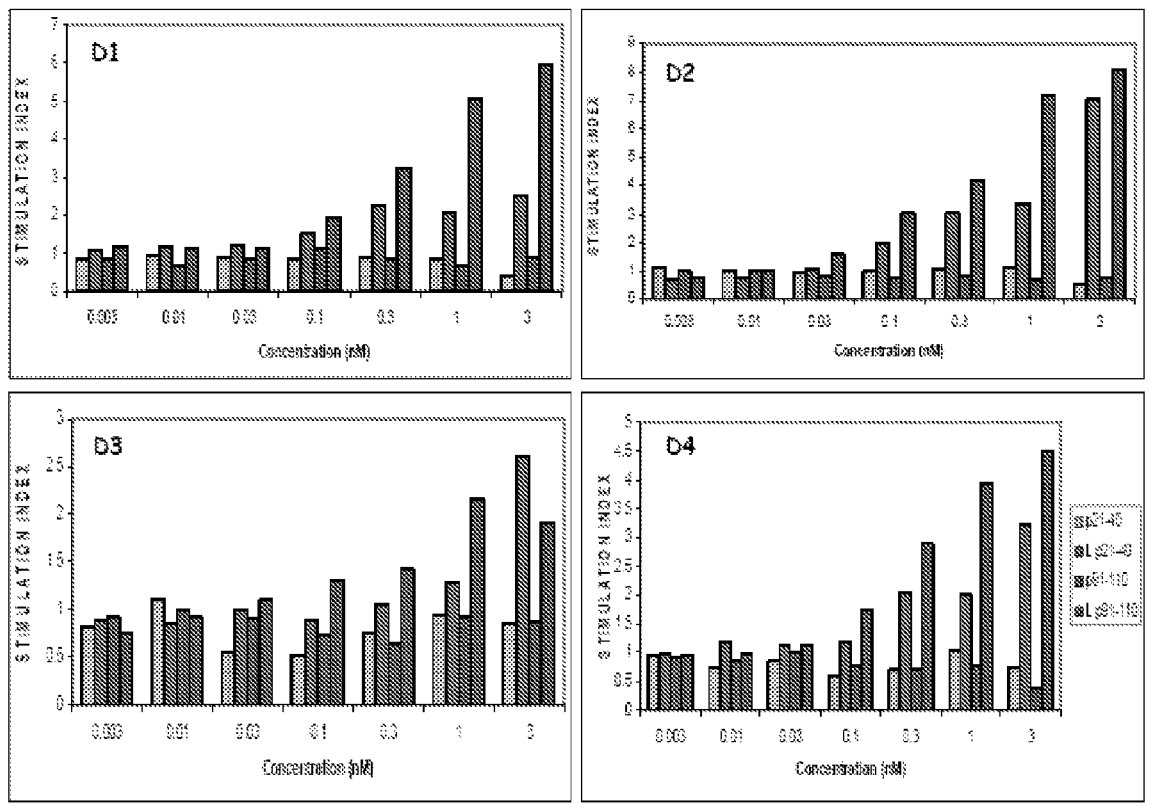
Figure 4A:
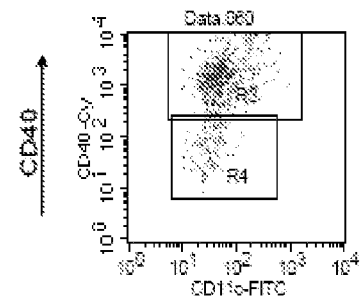
Figure 4A:
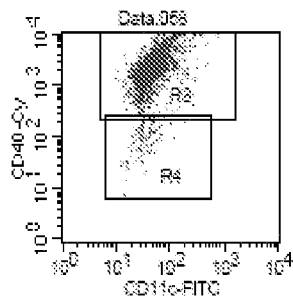
Figure 4A:
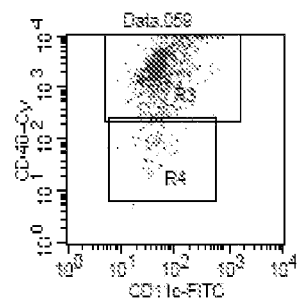
Figure 4A:
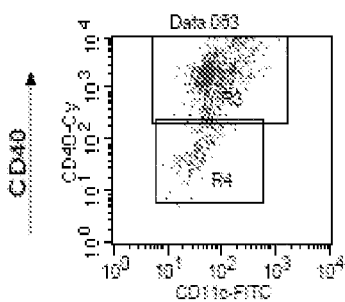
Figure 4A:
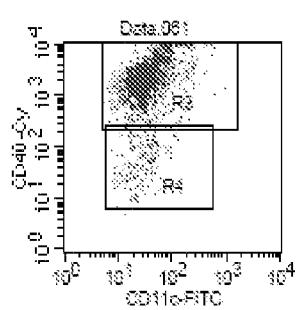
Figure 4A:
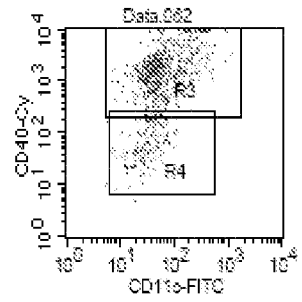
Figure 4B:
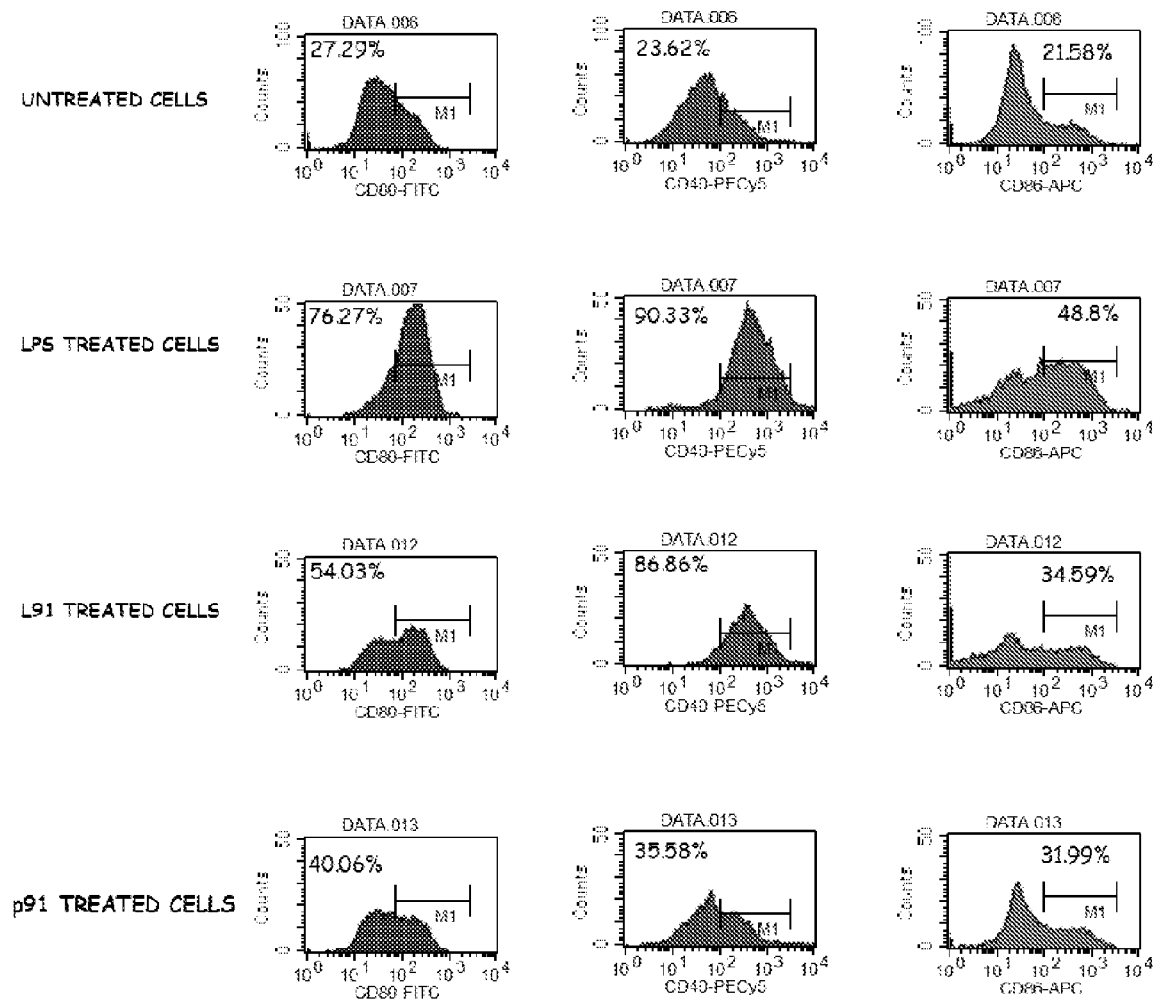
Figure 4C:
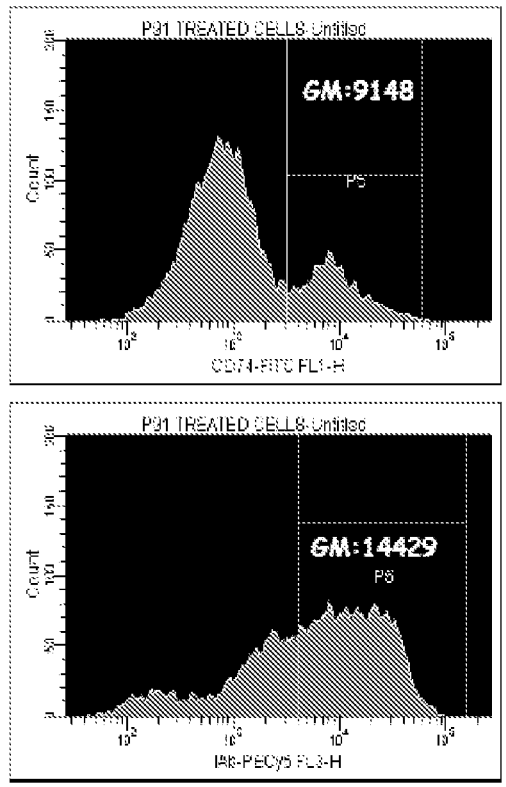
Figure 4C:
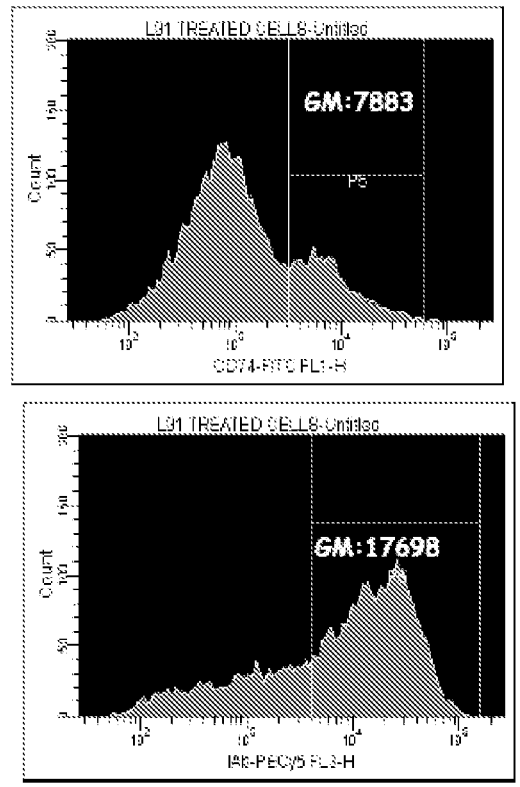

FIG. 3. Effect of promiscuous peptides/epitopes on the peripheral blood mononuclear cells obtained from different PPD$^+$ human subjects. Human peripheral blood mononuclear cells (PBMCs) were isolated from four healthy human donors (D1, D2, D3, D4) and they were stimulated in vitro using different concentration (0.003-3 nanomoles) of lipidated (Lp21-40, Lp91-110) and non lipidated (p21-40, p91-110) immunogenic constructs. T cell proliferation was measured by incorporating $^3$H-thymidine after 48 hrs.

FIG. 4. Lipidated peptides [immunogens] enhance DC maturation. (A) BALB/c mice were immunized with lipidated peptides [immunogen] and free peptides. Total splenocytes were recovered and in vitro stimulated with the lipidated and free peptides. After 48 hrs of incubation, they were harvested and stained for DC population (CD11c$^+$/CD40$^+$). CD11c$^+$/CD40$^+$ population indicates mature DCs. Lipidated immunogen constructs were able to induce DC maturation compared to their unlipidated counterparts. (B) Bone marrow derived DCs from C57BL/6 mice were cultured using standard protocol. On day 7 of culture they were treated with free or lipidated peptides for 12 hrs and then the cells were harvested and stained for activation markers. There was enhanced expression of CD80, CD86, CD40 in L91 treated cells compared to p91 treated cells. (C) On day 7 of culture, bone marrow derived DCs were treated with free or lipidated peptides for 12 hrs. Later on, the cells were harvested and stained for CD74 (immature MHC) and IA$^b$ (mature MHC). There was enhanced expression IA$^b$ and decrease in expression of CD74 when treated with L91 compared to free peptide GM indicates geometric mean fluorescent intensity.

Figure 5A:
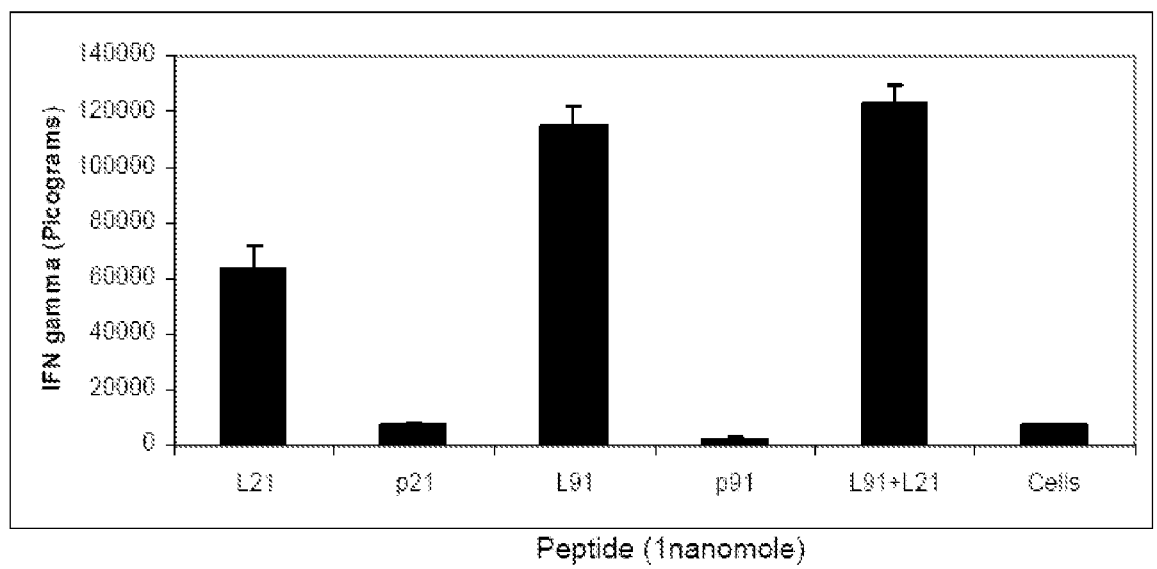
Figure 5B:
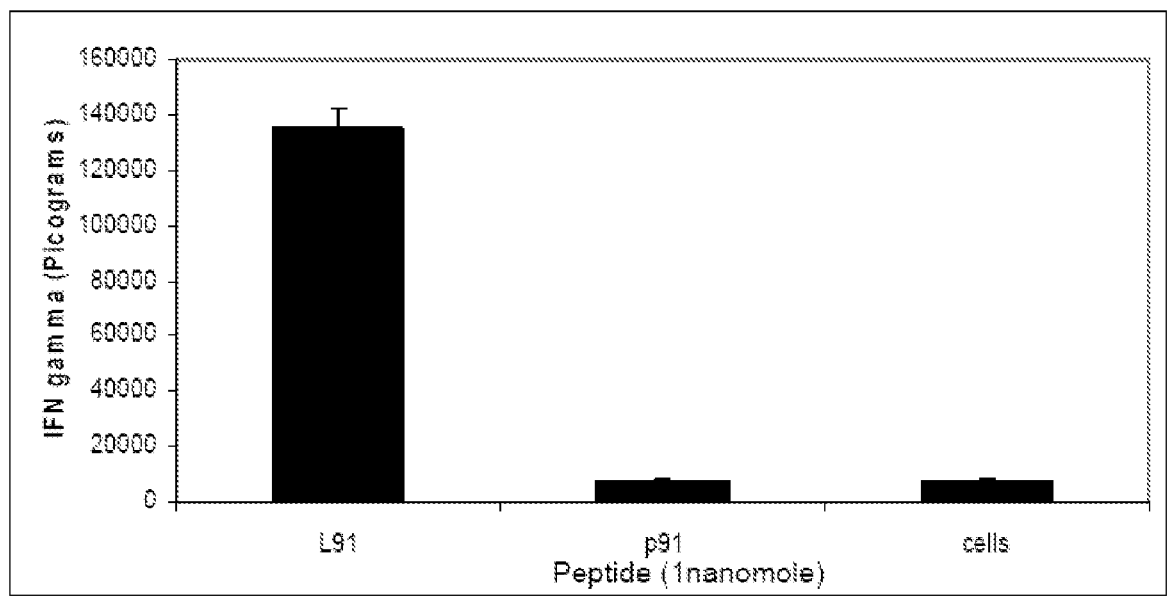

FIG. 5. Lipidated peptides [developed immunogen] induce the production of IFNγ in T cells. (A) Gamma irradiated $M. tuberculosis$ was injected in mice and splenocytes were in vitro challenged with developed immunogens for 48 hrs. Later on, levels of IFN-γ were estimated from the culture supernatants by ELISA. Lipidated peptides induced significantly higher IFN-γ production compared to free peptides. This indicates a Th1 phenotype of these cells. (B) Lipidated peptide L91 was injected in mice and splenocytes were in vitro challenged with constructs for 48 hrs. Later on, levels of IFNγ were estimated from the culture supernatants by ELISA. Lipidated peptides induce significantly higher IFN-γ production compared to free peptides and this indicates a Th1 phenotype of these cells.

Figure 6:
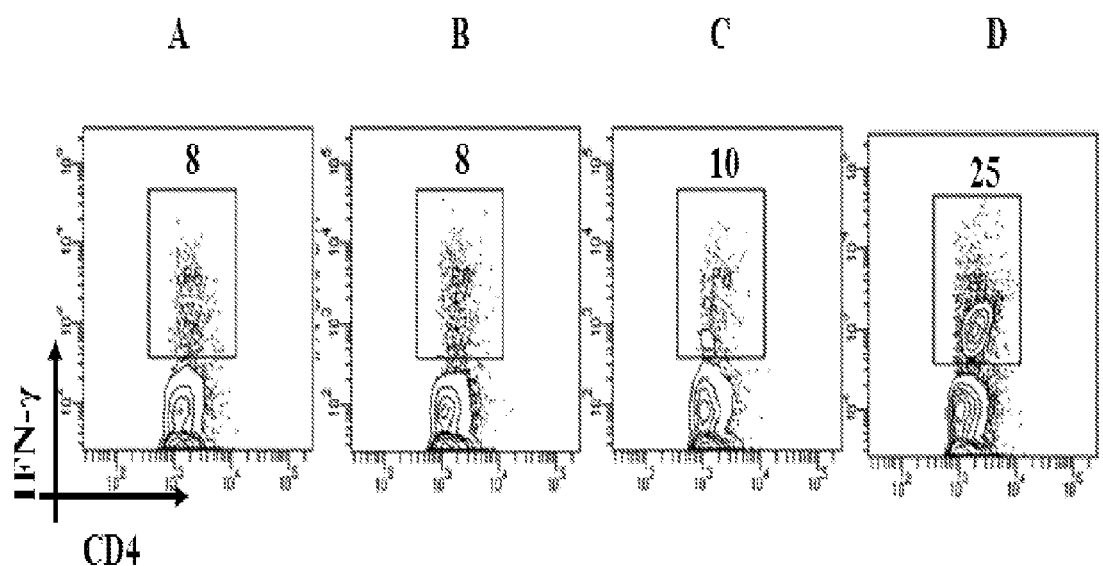

FIG. 6. CD4 T cells from mice immunized with immunogen containing SEQ ID No. 1 produced IFN-γ on in vitro peptide restimulation. Mice were immunized with lipopeptide containing SEQ ID No. 1. Splenocytes from the immunized mice were cultured with A) medium; B) Pam2Cys; C) non-lipidated peptide (SEQ ID No. 1); D) lipopeptide (containing SEQ ID No. 1) for 48 hrs. Cells were restimulated for 6 h and stained for surface CD4 and intracellular for IFN-γ. Representative flow cytometry contours depict IFN-γ producing CD4 T cells and numbers indicate their percentage.

Figure 7:
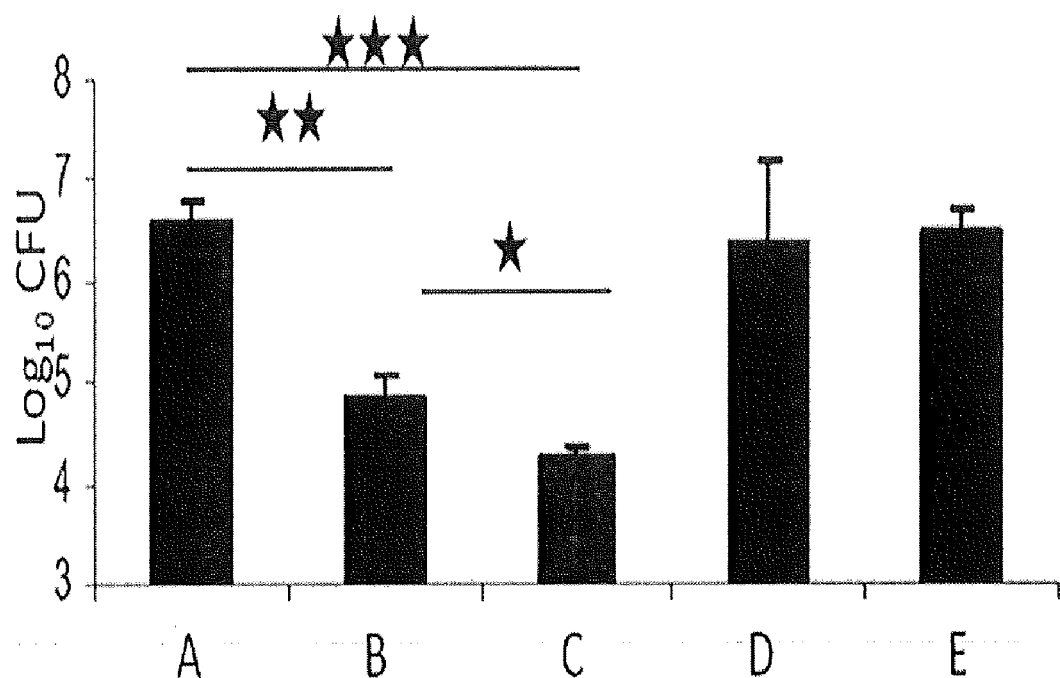

FIG. 7. The developed immunogen imparts better protection than BCG. The protection studies in mouse model were performed as described. Mycobacterial load in lungs was enumerated by CFU plating. Results are depicted as bar graphs with mean±SD (log$_{10}$ value). Mice were immunized with A) PBS; B) BCG; C) immunogen containing SEQ ID No. 1. D) non-lipidated peptide (Sequence ID No. 1); E) un-related lipopeptide containing peptide from influenza hemagglutinin virus. '*' indicates $p<0.05$, '' $p<0.01$, '*' $p<0.001$.

Figure 8:
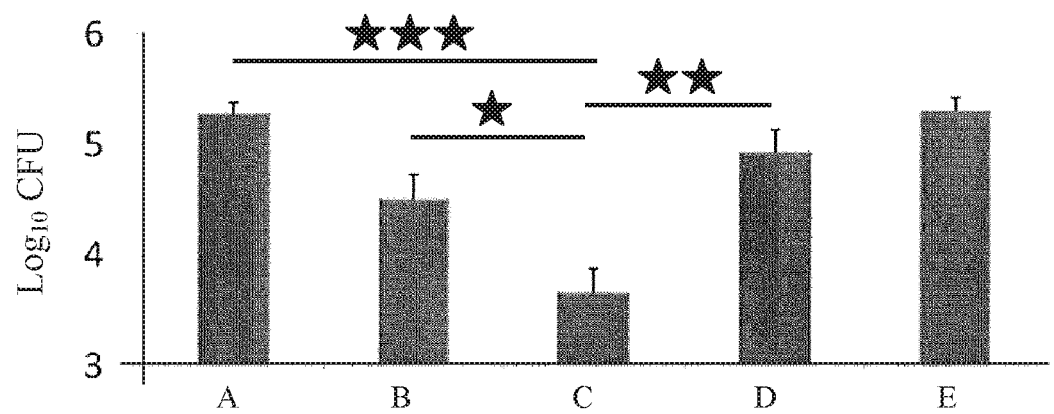

FIG. 8. Immunization with developed immunogenic lipopeptide results in protection against $M. tuberculosis$ in guinea pigs. The protection studies in guinea pig model were performed as described. Mycobacterial load in lungs was enumerated by colony forming units (CFU) plating. Results are depicted as bar graphs with mean±SD (log$_{10}$ value) Animals were immunized with A) PBS; B) BCG; C) immunogen containing SEQ ID NO. 1; D) non-lipidated peptide (Sequence ID No. 1); E) un-related lipopeptide from influenza hemagglutinin virus. '*' indicates $p<0.05$, '' $p<0.01$, '*' $p<0.001$.

Figure 9:
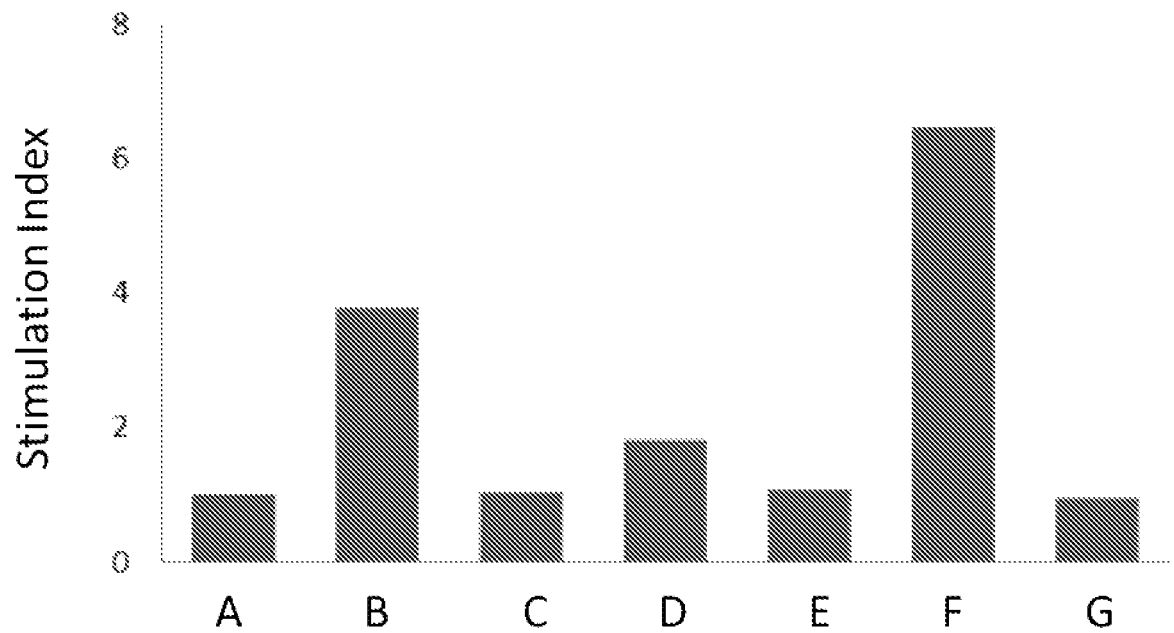

FIG. 9. The developed immunogenic lipopeptide induces proliferation of human peripheral blood mononuclear cells. Human peripheral blood mononuclear cells were obtained from sputum positive tuberculosis patient and incubated with A) medium alone; B) immunogen (containing the SEQ ID NO. 1); C) non-lipidated peptide (SEQ ID NO. 1); D) immunogen (containing the SEQ ID NO. 103); E) non-lipidated peptide (SEQ ID NO. 103); F) immunogen (containing both the sequences SEQ ID NO. 1 and SEQ ID NO. 103); G non-lipidated peptide (containing both the sequences SEQ ID NO. 1 and SEQ ID NO. 103) for 48 h. T cell proliferation was measured with $^3$H-thymidine incorporation.

DETAILED DESCRIPTION OF THE INVENTION

Abbreviations Used

TB: tuberculosis, $M. tuberculosis$: Mycobacterium tuberculosis
BCG: Bacillus Calmette-Guérin
TLR: Toll like receptor
HLA: Human leukocyte antigen
MHC: Major histocompatibility complex
DC: Dendritic cells
APC: Antigen Presenting Cells
L21: immunogen wherein X$_1$=SEQ ID. No. 2 and X$_2$=0
L91: immunogen wherein X$_1$=SEQ ID. No. 1 and X$_2$=0
p21: promiscuous epitope represented by SEQ ID No. 2
p91: promiscuous epitope represented by SEQ ID No. 1
PBMC: Peripheral Blood Mononuclear Cells
PBS: phosphate buffered saline
PPD$^+$: Purified protein derivative
Pam2Cys: S-[2,3-bis(palmitoyloxy) propyl]cysteine
BMDCs: bone marrow derived DCs
Ab: antibodies
p.i.: post-immunization.

The terms "peptides" and "epitopes" from $M. tuberculosis$ have been used interchangeably in the invention.

The present invention exploits promiscuous peptides from $M. tuberculosis$ and the biology of TLR ligands [TLRs] to design a synthetic immunogen wherein promiscuous CD4 and/or CD8 peptides/epitopes are physically associated with TLR ligands (TLR1 to TLR13) via a lysine and/or serine linker. These are prepared in a pharmaceutically administrable form either by covalent coupling or by encapsulating them in synthetic nanoparticles or liposomes that would ultimately be effectively presented by antigen presenting cells; especially dendritic cells to helper and cytotoxic T cells. Optionally, the said immunogen is also prepared in a vaccine form by combining it with pharmaceutically acceptable carriers, diluents or additives. Promiscuous peptides from $M. tuberculosis$ proteome were identified using in silico tools and/or experimental methods and were found to be 103 in number, which are enlisted in Table 1 illustrating the SEQ IDs and sequences of all the 103 CD4 and CD8 promiscuous epitopes of *M. tuberculosis* used in the invention. Then the identified peptides were either covalently coupled to TLR ligands that are amenable to such coupling followed by mixing and/or encapsulation in synthetic nanoparticles and liposomes.

The promiscuous T cell epitopes that are used as selective examples in the patent application have been identified employing peptide binding assays (using a reference binding peptide) and/or T cell proliferation and IFN-γ, IL-2, IL-4 secretion (Agrewala J N, Deacock S, Jurcevic S, Wilkinson R. Peptide recognition by T-cell clones of an HLA-DRB1*1501/*0901 heterozygous donor is promiscuous only between parental alleles. Peptide recognition by T-cell clones of an HLA-DRB1*1501/*0901 heterozygous donor is promiscuous only between parental alleles. Hum Immunol. 1997 June; 55(1):34-8; Agrewala J N, Wilkinson R J. Differential regulation of Th1 and Th2 cells by p91-110 and p21-40 peptides of the 16-kD alpha-crystallin antigen of *Mycobacterium tuberculosis*. Differential regulation of Th1 and Th2 cells by p91-110 and p21-40 peptides of the 16-kD alpha-crystallin antigen of *Mycobacterium tuberculosis*. Clin Exp Immunol. 1998 December; 114(3):392-7; Agrewala J N, Wilkinson R J. Influence of HLA-DR on the phenotype of CD4+T lymphocytes specific for an epitope of the 16-kDa alpha-crystallin antigen of *Mycobacterium tuberculosis*. Influence of HLA-DR on the phenotype of CD4+T lymphocytes specific for an epitope of the 16-kDa alpha-crystallin antigen of *Mycobacterium tuberculosis*. Eur J Immunol. 1999 June; 29(6):1753-61; Weichold F F, Mueller S, Kortsik C, Hitzler W E, Wulf M J, Hone D M, Sadoff J C, Maeurer M J. Impact of MHC class I alleles on the *M. tuberculosis* antigen-specific CD8+T-cell response in patients with pulmonary tuberculosis. Genes Immun. 2007, 8(4):334-43). The listed peptide sequences were predicted computationally using the IEDB prediction servers and were selected on the basis of binding cut off of IC50<500 and the ability of peptides to bind to a minimum of three HLA alleles. A few peptides were also selected based on the in vitro binding assays and CD8 T cell lysis assays (Axelsson-Robertson R, Weichold F, Sizemore D, Wulf M, Skeiky Y A, Sadoff J, Maeurer M J. Extensive major histocompatibility complex class I binding promiscuity for *Mycobacterium tuberculosis* TB10.4 peptides and immune dominance of human leucocyte antigen (HLA)-B*0702 and HLA-B*0801 alleles in TB10.4 CD8 T-cell responses. Immunology. 2010 April; 129(4):496-505; Masemola A M1, Mashishi T N, Khoury G, Bredell H, Paximadis M, Mathebula T, Barkhan D, Puren A, Vardas E, Colvin M, Zijenah L, Katzenstein D, Musonda R, Allen S, Kumwenda N, Taha T, Gray G, McIntyre J, Karim S A, Sheppard H W, Gray C M. Novel and promiscuous CTL epitopes in conserved regions of Gag targeted by individuals with early subtype C HIV type 1 infection from southern Africa. J Immunol. 2004 Oct. 1; 173(7):4607-17). The sequences of the promiscuous peptides/epitopes from *M. tuberculosis* which were tested in the aforesaid manner are represented by SEQ ID Nos. 1 to 103 [Table 1].

Covalent Coupling of TLR Ligands to Promiscuous Peptides:

The peptides/epitopes represented by SEQ ID Nos. 1 to 103 were synthesized using standard Fmoc techniques. If the construct has two or more peptides, they were linked with a lysine residue and then two serine residues were added to enhance immunogenecity and also for enabling the peptides to be linked to the TLR ligands. The peptides (along with the serine linker) were coupled to the TLR ligand using an established methodology (Jackson D C, Lau Y F, Le T, Suhrbier A, Deliyannis G, Cheers C, Smith C, Zeng W, Brown L E. A totally synthetic vaccine of generic structure that targets Toll-like receptor 2 on dendritic cells and promotes antibody or cytotoxic T cell response. 2004, Proc Natl Acad Sci USA. 101:2004:15440-5). In short, excess of synthetic TLR ligand, O_benzotriazole-N,N,N_,N_-tetramethyluronium-tetrafluoroborate, and 1-hydroxy benzotriazole were dissolved in dichloromethane [DCM], and a 3-fold excess of diisopropylethylamine was added. Then this solution was added to resin bound peptide (pre-synthesized) to generate the lipopeptide, which was cleaved from the resin and purified using reverse phase chromatography. Two serine residues were added following the peptide to increase the immunogenecity of the immunogen.

The above prepared immunogen was bound to TLRs expressed on the surface of APCs and to MHC class I and II molecules. The triggering of the TLRs resulted in maturation of the APCs and upregulation of costimulatory molecules and cytokines. The matured APCs effectively present the peptides to $CD4^+$ and $CD8^+$ T cells and elicit a robust immune response against *M. tuberculosis* (FIG. 1). This strategy can be used directly in vivo or alternatively the DCs can be pulsed and triggered with this immunogen in vitro and can be adoptively transferred to the host for inducing protective immunity.

Encapsulation of the Peptides and TLR Ligands:

Encapsulation is performed where covalent coupling is not amenable, as in the case of nucleic acids (ligands for TLRs 3, 7, 9) and when the TLR ligands are predominantly intracellular. However, the same strategy can be applied to TLRs 2, 4 and 5 because they are also expressed in the endosomal compartments. Promiscuous CD4 and CD8 epitopes from *M. tuberculosis* were mixed with TLR ligands like nucleic acids that cannot be covalently coupled to these peptides or the covalently coupled TLR2, 4 ligands—promiscuous epitopes were encapsulated with poly γ-glutamic acid, poly(d,l-lactic-co-glycolic acid), poly(ethylene glycol)dimethacrylate, 2-diethylamino ethyl methacrylate, aminoethyl methacrylate, methyl methacrlate etc. in the form of nanoparticle like complexes for the uptake by dendritic cells.

Moreover, this strategy can be specially modified to target dendritic cells. All APCs can take up antigen avidly. Among the APCs, dendritic cells can take up large sized particles up to 500-700 nm in diameter. However, for the effective immunization of antigens encapsulated in nanoparticles, the size should not be more than 200 nm. Hence for direct immunization, 200 nm diameter particles and for in vitro addition of encapsulated material and then adoptive transfer in to living systems, 500 nm encapsulated particles would be ideal. Promiscuous CD4 and CD8 T cell epitopes from *M. tuberculosis* were mixed with TLR ligands like nucleic acids that cannot be covalently coupled to these peptides and the covalently coupled TLR-2, TLR-4 ligands—promiscuous epitopes were encapsulated in the form of nanoparticles like complexes for the uptake by dendritic cells.

The APCs will take up the encapsulated constructs avidly and once it reaches the endosomal compartments, the TLR ligands will activate the APCs and the CD4 T cell epitopes will be loaded on to the MHC II molecules and presented to CD4 T cells. CD8 T cell epitopes will be loaded on to MHC I molecules and will elicit effective CD8 T cell priming and would eventually lead to a robust CD4 and CD8 T cells response.

Based on the data, lipidated promiscuous peptides, give robust T cell response in many strains of mice (FIG. 2). Moreover, it is also able to circumvent HLA restriction in humans (FIG. 3). Further, it enhances DC maturation and predominantly results in Th1 response (FIGS. 4, 5).

Using this strategy, effective immune response can be generated against many pathogenic organisms and an array of diseases like cancer, allergies.

EXAMPLES

The following examples are given by way of illustration only and therefore should not be construed to limit the scope of the present invention.

Experimental Animals.

6-8 weeks old female BALB/c, C3He, and C57BL/6 mice were used for the experiments. All experiments were carried out on BALB/c, unless mentioned. Female Duncan-Hartley Guinea pigs (6-8 weeks old) were used for protection studies. Animals were housed in Biosafety Level-3 facility of Institute of Microbial Technology, Chandigarh and National JALMA Institute for Leprosy and Other Mycobacterial Diseases (NJIL & OMD), Agra, India. Animals were offered ad libitum pellet feed and water.

Patients and Healthy Volunteers.

PBMCs were separated from the blood of the sputum positive pulmonary tuberculosis patients and PPD$^+$ healthy volunteers.

Immunization.

Mice were immunized with the developed immunogenic lipopeptides (20 nmol/animal). Twenty-one days later, a booster dose (10 nmol) was administered. Animals were sacrificed 45 days post booster immunization.

For long-term T cell memory and protection studies, lipopeptides or control non-lipidated peptides were immunized (20 nmol/mouse or 100 nmol/Guinea pig) intraperitonially, and 21 days later, a booster (10 nmol/mouse and 50 nmol/Guinea pig) was inoculated. For comparison, animals were immunized with BCG (1×10$^6$ CFU/animal). The animals were rested for 75 days before aerosol challenge with live *M. tuberculosis*. The animals were sacrificed 30 days post-challenge.

Example 1

Synthesis of Lipidated Peptides

The synthesis, purification, and characterization of peptides and lipopeptides were done as per the procedure detailed below:

To enable lipid attachment between the CD4 T cell epitopes and CD8 T cell epitopes, F-moc-lysine (Mtt)-OH was inserted at a point between the two epitopes in the approximate center of the resin-bound peptide. Following completion of peptide synthesis, the Mtt group was removed by continual flow washing with 1% TFA in DCM over a period of 30-45 min. Pam2Cys was then coupled to the exposed ε-amino group according to the procedure described previously (Zeng W, Jackson D C, Rose K J. Synthesis of a new template with a built-in adjuvant and its use in constructing peptide vaccine candidates through polyoxime chemistry Pept Sci. 1996 January-February; 2(1):66-72). The presence of serine between the Pam2Cys and peptide moieties improves immunogenicity. Hence, two residues of serine were incorporated between the peptide and lipid moieties of the Pam2Cys-containing peptide immunogen. This was simply done by sequential addition of two serine residues to the peptide before covalent attachment of the lipid moiety.

Employing this methodology, constructs that contained single promiscuous CD4 or CD8 T cell epitopes or containing both CD4 and CD8 T cell epitopes were synthesized. The immunogenicity was experimentally validated in mice, guinea pigs and with human lymphocytes.

It was found that although the use of an automatic synthesizer can save time and be relatively unproblematic for simple sequences, the synthesis of peptides manually allows for more flexibility and control over the assembly process. This is particularly important for the synthesis of difficult sequences as it permits quick and easy intervention at any point. The apparatus routinely used in this laboratory for the manual synthesis of peptides consists of a flask attached to a glass manifold that can support up to four sintered funnels, thereby permitting the simultaneous synthesis of up to four peptides. The side arm of the flask is attached to a vacuum pump to allow for solvents to be aspirated from each funnel. The manifold also contains valves that are arranged so that a vacuum can be applied universally either to all four funnels or restricted to individual funnels.

There are a very large number of choices of solid phase supports available for peptide synthesis, and the prospective peptide chemist should spend a little time familiarizing themselves with the possibilities: For the purposes of the T-helper cell epitopes designed to bind MHC II and cytotoxic T-cell epitopes designed to fit in the groove of MHC I molecules, however, resins should be used to assemble peptides containing a free carboxyl, COOH group, at the C-terminus (i.e.; Tentagel S PHB resin, Rapp Polymere).

For the synthesis of immunogen comprising SEQ ID No. 1 [SEFAYGSFVRTVSLPVGADE]-K-SEQ ID No. 2 [FVRSSNLKF], weighed 1 g Tentagel S RAM resin into a sintered funnel and allowed to swell in DMF at room temperature for at least 30 min.

1. To expose the Fmoc-protected NH2 group on the resin, treated with either piperidine or 2.5% DBU in DMF for 2×5 min, followed by four washes with DMF.
2. Weighed 0.92 mmol of Fmoc-amino acid (i.e., a fourfold excess of amino acid relative to the substitution level of the support) into clean and dry plastic tubes (Sarstedt, Germany); [Tubes with a 10-mL volume capacity are ideal]. Added an equimolar amount of HOBT and HBTU relative to the amount of amino acid to 2 mL of DMF and a six-fold excess of DIPEA over the substitution level of the solid phase support. Dissolved fully by vortexing and sonication.
3. Removed DMF from the swollen resin in the glass sinter filter funnel by aspiration using the vacuum pump and added the activated amino acid solution. Stirred with a spatula and incubated at room temperature for 30-45 min, stirring occasionally.
4. After 30-45 min, aspirated the amino acid solution followed by two washes of the resin with DMF.
5. Transferred a few beads of resin with a Pasteur pipette into an Eppendorf tube and added two drops of DIPEA followed by five drops of TNBSA solution. Inspected the beads by eye or under a microscope. If the beads were colorless after 1 min, then acylation was complete and the next step was carried out. Any trace of orange color in the beads indicates the presence of free amino groups and incomplete coupling. In those cases steps 2-5 should be repeated until a negative TNBSA test is returned.
6. Removed the N-Fmoc group of the coupled amino acid by carrying out step 1. Confirmation of the removal of the Fmoc group was determined by performing a TNBSA test that resulted in a positive orange color change.
7. Repeated steps 2-6 with the next amino acid until completion of the SEQ ID. No. 103.

8. To enable lipid attachment, repeated steps 3-6 using (Fmoc)-K(Mtt)-OH to enable lipid attachment between the two epitopes.
9. Repeated steps 2-6 with the amino acids corresponding to the SEQ ID. No. 1.
10. Repeated steps 3-6 using (Boc)-Gly-OH to temporarily block the N-terminus of the peptide. The Boc-protective group is resistant to removal by the conditions used for lipid attachment until cleavage of the assembled product from the resin and concomitant removal of the side-chain-protecting groups.
11. At this point, the completed peptide on resin was washed sequentially in DMF, DCM, and methanol, dried under vacuum, and stored in a desiccated atmosphere at room temperature until ready to be cleaved for use as a non-lipidated peptide control.
12. Continuing from step 11, the resin was treated with 1% TFA in DCM5×12 min to remove the Mtt group from the side chain of the lysine residue situated between the two epitopes.
13. Repeated steps 2-6 in order to couple the two serines to the exposed ε-amino group of the intervening lysine residue and removed the Fmoc group from the second serine residue. The peptide is now ready for lipid attachment.

Attachment of the TLR ligand Pam2Cys to Peptide

Synthesis of S-(2,3-dihydroxypropyl) Cysteine

1. Triethylamine (6 g, 8.2 mL, 58 mmol) was added to 1-cysteine hydrochloride (3 g, 19 mmol) and 3-bromo-propan-1,2-diol (4.2 g, 2.36 mL, 27 mmol) in water. This homogeneous solution was kept at room temperature for 3 d.
2. The solution was reduced in vacuum at 4 degree C. to a white residue which was washed three times with acetone and dried to give S-(2,3-dihydroxypropyl) cysteine as a white amorphous powder (2.4 g, 12.3 mmol, 64.7%). This product was used for the next step without further purification.

Synthesis of N-Fluorenylmethoxycarbonyl-S-(2,3-dihydroxypropyl) Cysteine (Fmoc-Dhc-OH)

1. Dissolved S-(2,3-dihydroxypropyl)cysteine (2.45 g, 12.6 mmol) in 20 ml of 9% sodium carbonate.
2. Added a solution of fluorenylmethoxycarbonyl-N-hydroxysuccinimide (3.45 g, 10.5 mmol) in acetonitrile (20 mL) and stirred the mixture for 2 hours. Diluted with water (240 mL), and extracted with diethyl ether (25 mL×3).
3. Acidified the aqueous phase to pH 2 with concentrated hydrochloric acid and then extracted with ethyl acetate (70 mL×3).
4. Washed the extract with water (50 mL×2) and saturated sodium chloride solution (50 mL×2). Dried over sodium sulfate and evaporated to dryness. Recrystallized from ether and ethyl acetate at minus 20 degree C. to yield a colorless powder (2.8 g, 6.7 mmol, 63.8%).

Coupling of Fmoc-Dhc-OH to Resin-Bound Peptide
1. Activated Fmoc-Dhc-OH (100 mg, 0.24 mmol) in DMF (3 mL) with HOBT (36 mg, 0.24 mmol) and DICI (37 mg or 0.29 mmol) at 0 degree C. for 5 min.
2. Added this mixture to a vessel containing the resin-hound peptide (0.06 mmol, 0.25 g amino-peptide resin). After shaking for 2 h removed the solution by filtration and washed the resin with DCM and DMF (3×30 mL). Completeness of the reaction was monitored using the TNBSA test.

Palmitoylation of the Two Hydroxy Groups of the Fmoc-Dhc-Peptide Resin
1. Dissolved palmitic acid (307 mg, 1.2 mmol), DICI (230 mg or 1.82 mmol) and DMAP (14.6 mg, 0.12 mmol) in 3 mL of DCM.
2. Suspended the resin-bound Fmoc-Dhc-peptide resin (0.06 mmol, 0.25 g) in the above solution and kept under shaking for 16 h at room temperature. Removed the supernatant by filtration and thoroughly washed with DCM and DMF to remove any residue of urea. The removal of the Fmoc group was accomplished with 2.5% DBU (2×5 min).

Cleavage of Lipopeptide from Solid Phase Support

This procedure simultaneously cleaves the lipopeptide or peptide from the solid phase support and removes side-chain-protecting groups from those amino acids that have them.
1. Transferred the vacuum-dried resin into a clean dry McCartney glass bottle and added 3 mL cleavage reagent (88% TFA, 5% phenol, 5% water, and 2% TIPS).
2. Gently flushed with nitrogen and left for at least 3 h with occasional mixing.
3. Transferred the mixture into the barrel of a 5-mL syringe plugged with non-adsorbent cotton wool and used the plunger to drive the peptide-containing supernatant into a clean dry 10-mL centrifuge tube.
4. Evaporated the solution to a volume of approximately 500 microL under a gentle stream of nitrogen.
5. Added 10 mL cold diethyl ether to the peptide, solution and vortexed vigorously to precipitate the peptide.
6. Centrifuged to sediment the peptide material, washed by aspirating the diethyl ether, and resuspended the precipitate in cold diethyl ether followed by washing twice in cold diethyl ether.
7. After the final wash, aspirated the remaining diethyl ether and allowed the pellet to dry in a fume hood for approximately 1 h.
8. Dissolved the precipitate in 0.1% aqueous TFA and lyophilized.
9. Assessed the product purity using reversed-phase chromatography and fidelity of the target sequence by mass spectrometry.

Briefly, T cell epitopes were conjugated to lipid moiety Pam2Cys, corresponding to the lipid component of macrophage-activating lipopeptide 2 (MALP-2) from mycoplasma. CD4 T cell promiscuous peptides represented by SEQ ID No. 1 to 98 were selected from the 16 kDa secretory protein of *M. tuberculosis* and conjugated to Pam2Cys to make immunogen L91. The CD8 promiscuous T cell epitopes represented by SEQ ID No. 99 to 103 were selected from antigen 85B of *M. tuberculosis*. The control lipopeptide was synthesized with an epitope from influenza hemagglutinin virus (HA) containing sequence KYVKQNTLKL. All the peptides were modified at the N-terminus with two serine residues followed by the lipid moiety Pam2Cys to obtain the synthetic lipopeptide.

Example 2

Protection Studies in Mice and Guinea Pigs

Animals were immunized as described above and rested for 75 days. They were then exposed to *M. tuberculosis* H37Rv through aerosol route at 100 CFU (mice) or 30 CFU (Guinea pigs) and sacrificed 30 days later. Mycobacterial burden in lungs was estimated by CFU plating. For histopathological analysis, formalin fixed tissues were processed and stained with hematoxylin and eosin.

Results

Immunization of Lipopetides Results in Robust Th1 Immune Response

Mice immunized with immunogenic lipopeptide containing SEQ ID No. 1, were rested for 45 days and checked for recall responses. Upon restimulation with peptides, predominant production of IFN-γ in CD4 T helper T cells (FIG. 6) was observed.

Immunization of Lipopeptides Results in Protection Against *M. tuberculosis* in Mice.

It was explored whether with prepared immunogen lipopeptide containing SEQ ID No. 1 (SEFAYGSFVRTVSLPVGADE), protection from experimental tuberculosis could be rendered. Mice were vaccinated with lipopeptide or controls (BCG, free peptide, un-related lipopeptide from influenza hemagglutinin, and placebo). Later, the mice were aerosol challenged with *M. tuberculosis* on day 75 post vaccination and sacrificed 30 days later. It was observed that mice immunized with immunogen lipopeptide containing SEQ ID No. 1 restricted the growth of mycobacterium significantly as compared to BCG ($p<0.05$) and other controls (FIG. 7).

Immunization with Lipopeptide Results in Protection Against *M. tuberculosis* in Guinea Pigs.

The next set of experiments was performed to demonstrate whether vaccination with immunogen lipopeptide containing SEQ ID No. 1 (SEFAYGSFVRTVSLPVGADE) could render protection from experimental tuberculosis in guinea pigs. Duncan-Hartley guinea pigs were vaccinated with prepared lipopeptide or controls (placebo, BCG, free peptide and unrelated lipopeptide from influenza hemagglutinin virus). Later, the animals were aerosol challenged with *M. tuberculosis* on day 75 post vaccination and sacrificed 30 days later. It was observed that animals immunized with immunogen lipopeptide containing SEQ ID No. 1 harbored significantly lower bacterial load in lungs as compared to BCG and other controls (FIG. 8).

Example 3

Aerosol Infection and Mycobacterial Burden in Lungs

Frozen stocks of *M. tuberculosis* H37Rv were thawed quickly at 37° C. and centrifuged at 10000×g for 10 min and washed 2× with PBS-Tween-80. Peptide/BCG/placebo immunized animals were challenged with a standardized low-dose of aerosol infection, using an inhalation exposure system (Glas-Col, Terre Haute, Ind.) to deposit approximately 100 (mice) or 30 (Guinea pigs) live bacteria in the lungs (as checked by CFU plating after 24 h of exposure). Thirty days post-infection, lungs were harvested and homogenized in 7H9 supplemented with Tween-80 (0.05%). Serially diluted homogenates of individual lungs were plated onto Middlebrook 7H11 containing thiophene carboxylic hydrazide (TCH, 2 μg/ml) and OADC. CFUs were counted after 3-4 weeks of incubation at 37° C.

Immunization of Lipopetides Results in Protection Against Tuberculosis in Mice.

It was explored whether with prepared immunogen lipopeptide containing SEQ ID No. 1 (SEFAYGSFVRTVSLPVGADE), protection from experimental tuberculosis could be rendered. Mice were vaccinated with lipopeptide or controls (BCG, free peptide, un-related lipopeptide from influenza hemagglutinin, and placebo). Later, the mice were aerosol challenged with *M. tuberculosis* on day 75 post vaccination and sacrificed 30 days later. It was observed that mice immunized with immunogen lipopeptide containing SEQ ID No. 1 restricted the growth of mycobacterium significantly as compared to BCG ($p<0.05$) and other controls (FIG. 7).

Immunization with Lipopeptide Results in Protection Against Tuberculosis in Guinea Pigs.

The next set of experiments were performed to demonstrate whether vaccination with immunogen lipopeptide containing SEQ ID No. 1 (SEFAYGSFVRTVSLPVGADE) could render protection from experimental tuberculosis in guinea pigs. Duncan-Hartley guinea pigs were vaccinated with prepared lipopeptide or controls (placebo, BCG, free peptide and un-related lipopeptide from influenza hemagglutinin virus). Later, the animals were aerosol challenged with *M. tuberculosis* on day 75 post vaccination and sacrificed 30 days later. It was observed that animals immunized with immunogen lipopeptide containing SEQ ID NO. 1 harbored significantly lower bacterial load in lungs as compared to BCG and other controls (FIG. 8).

Example 4

Isolation of Lymphocytes from Spleen

Spleens were removed aseptically and single cell suspensions were prepared. RBCs were lysed by ACK lysis buffer ($NH_4Cl$ 0.15M, $KHCO_3$ 10 mM, EDTA 88 μM), washed thrice with PBS and resuspended in complete medium [CM; RPMI-1640 containing FBS-10%]. Splenocytes ($2\times10^5$/well) were cultured in 96 well U bottom plates for 48-72 h. Different concentrations of peptides were added to the cultures. A pretitrated dose (50 or 100 ng/ml) of commercially available ultrapure Pam2Cys (Invivogen) was used as controls.

Lymphocytes from lipopeptide immunized mice responded to the recall stimulation with peptides effectively through T cell proliferation and IFN-γ secretion (FIGS. 2 and 5B).

Example 5

Proliferation Assays

T cell proliferation assays were set by incubating human PBMCs or mouse splenocytes with peptides for 72 h and 48 h respectively. Later, [$^3$H]-thymidine (0.5 μCi/well) was incorporated. After 16 h, plates were harvested and radioactivity incorporated was measured. Cell proliferation assays were set as described previously (Singh V, Jain S, Gowthaman U, Parihar P, Gupta P, Gupta U D, Agrewala J N. Co-administration of IL-1+IL-6+TNF-α with *Mycobacterium tuberculosis* infected macrophages vaccine induces better protective T cell memory than BCG. PLoS One. 2011 Jan. 19; 6(1)). Briefly, lymphocytes ($2\times10^5$ cells/well) isolated from spleen and/or lymph nodes were cultured in triplicates in 200 μl of complete RPMI-1640 with different concentrations of L91/F91 in 96 well U bottom plates. After 48 h and 72 h, the cultures were pulsed with 0.5 μCi of [$^3$H]-thymidine. The plates were harvested after 16 h using Tomtec-Harvester-96 (Tomtec, Hamden, Conn.). Radioactivity incorporated was measured by Wallac 1450 Microbeta Trilux β-scintillation counter (Perkin Elmer, Waltham, Mass.). For human lymphoproliferation, Blood (20 ml) was drawn in vacutainers from $PPD^+$ volunteers or sputum positive tuberculosis patients. Peripheral mononuclear cells (PBMCs) were isolated by density gradient method using Histopaque-1077 following manufacturer's instructions. Purified PBMCs were washed 4× in PBS containing 1% FBS. Cells ($2\times10^5$ cells/well) were cultured in triplicates with CM (without 2-mercaptoethanol), in U-bottom 96 w plates with peptides. Cells were incubated for 72 h and later pulsed with 0.5 μCi of [$^3$H]-thymidine. The plates were harvested after 16 h, as mentioned above.

The influence of lipopeptides in stimulating peripheral blood mononuclear cells of tuberculosis patient is illustrated in FIG. 9. Immunogenic lipopeptide containing SEQ Id No. 1 (SEFAYGSFVRTVSLPVGADE) enhanced the proliferation of human PBMCs as compared to non-lipidated peptide counterparts. Interestingly, it was observed that the best response was obtained with the lipopeptide immunogen constructs that contained both the CD4 helper epitope (SEQ ID No. 1) and the CD8 cytotoxic epitope (SEQ ID No. 103).

Example 6

Intracellular Staining

Lymphocytes (2×10$^6$ cells/ml) were cultured with peptides in triplicates in 96 w plate for 48 h. Cells were pooled and washed twice with wash buffer (PBS containing FBS-1%). Cells were re-stimulated with PMA (50 ng/ml) and ionomycin (1 μg/ml) for 6 h/37° C. and in the last 4 h brefeldin A (10 μg/ml) was added in cultures. After 6 h of activation, cells, were washed twice with staining buffer (BSA-1%, $NaN_3$-0.01% in PBS). Fc receptors were blocked with 2.4 G2 and then stained with anti-mouse fluorochrome labeled mAbs for CD4. Cells were washed twice with staining buffer and fixed in paraformaldehyde-2%. Then they were permeabilized with saponin-0.01% in PBS-FCS-1% (permeabilization buffer). This was followed by incubation with fluorochrome labeled anti-cytokine Abs (or its isotype control) in permeabilization buffer staining buffer containing (saponin—0.01%). The incubation period for each step was 30 min/4° C. or otherwise mentioned. Finally, cells were fixed in parafolmaldehyde-1% and acquired on FACS Aria II and data was analyzed by FACS DIVA (BD Biosciences, San Jose, Calif.).

Lymphocytes from lipopeptide immunized mice responded to the recall stimulation with peptides effectively through secretion IFN-γ (FIGS. 6A-D). Notably, the secretion of IFN-γ was specific to CD4 T cells. Pam2Cys alone in absence of the peptide component did not elicit production of IFN-γ in CD4 T cells.

Statistical Analysis.

Data were analyzed by unpaired students 't' test and Student-Newman-Keuls multiple comparisons test by GraphPad InStat 3 software.

Advantages of the Invention

- The epitopes are precisely defined; can avoid autoreactive portions in the antigen
- Requires no extensive processing
- The developed immunogen does not require any adjuvant
- Totally synthetic
- Can activate both CD4 and CD8 T cells
- Skews immune response to Th1 type
- Can activate naïve T cells
- Can induce the generation of long-lasting memory T cells
- Can reduce the bacterial burden from pulmonary and extra-pulmonary regions of the body

TABLE 1

Sequence ID Numbers and the respective sequences LIST of promiscuous epitopes [peptides] used

| Sl. No. | Sequence ID. No. | Promiscuous CD4 epitopes from *M. tuberculosis* |
|---|---|---|
| 1 | SEQ ID No. 1 | SEFAYGSFVRTVSLPVGADE |
| 2 | SEQ ID No. 2 | LFAAFPSFAGLRPTFDTRLM |
| 3 | SEQ ID No. 3 | TYGIASTLLGVLSVAAV |
| 4 | SEQ ID No. 4 | VVEKLRTHSSGRIEA |
| 5 | SEQ ID No. 5 | QTVHWNLRLDVSDVD |
| 6 | SEQ ID No. 6 | LLAVLIALALPGAAV |
| 7 | SEQ ID No. 7 | PISGLQAIGLMQAVQG |
| 8 | SEQ ID No. 8 | TLVQIIRWLRPGAVIAI |
| 9 | SEQ ID No. 9 | GYKVFPVLNLAVGGSG |
| 10 | SEQ ID No. 10 | LRQRISQQLFSFGDPT |
| 11 | SEQ ID No. 11 | ILRAGAAFLVLGIAAATF |
| 12 | SEQ ID No. 12 | RYMIDFNNHANLQQA |
| 13 | SEQ ID No. 13 | FAWVNHMKIFFNNKGVVAKGT |
| 14 | SEQ ID No. 14 | QWGSLPSLRVYPSQV |
| 15 | SEQ ID No. 15 | FLQRNLPRGTTQGQAFQFLGAAIDH |
| 16 | SEQ ID No. 16 | AKVVVVGGLVVVLAVVAAAA |
| 17 | SEQ ID No. 17 | LYRKLTTTTVVAYFS |
| 18 | SEQ ID No. 18 | DKVQIMGVRVGSIDK |
| 19 | SEQ ID No. 19 | VTLHYSNKYQVPATATA |
| 20 | SEQ ID No. 20 | LVASRTIQLSPPYTG |
| 21 | SEQ ID No. 21 | DFVAITRSLALFVSA |
| 22 | SEQ ID No. 22 | TALHVLPTYASNFNNL |
| 23 | SEQ ID No. 23 | PIQLICSAIQAGSRL |
| 24 | SEQ ID No. 24 | ALKFNYLPFGSNPFSS |
| 25 | SEQ ID No. 25 | VLLDANVLIALVVAEH |
| 26 | SEQ ID No. 26 | SLVRFLVRSGQSAAAAR |
| 27 | SEQ ID No. 27 | MTARSVVLSVLLGAHPA |
| 28 | SEQ ID No. 28 | VRSADGYRLSDRLLAR |
| 29 | SEQ ID No. 29 | WHMLIVTSIGTDART |
| 30 | SEQ ID No. 30 | FVVAAAMVRHLLTDPML |
| 31 | SEQ ID No. 31 | MVLRSRKSTLGVVVCLALVLGGP |
| 32 | SEQ ID No. 32 | SLRVSWRQLQPTDPRTLP |
| 33 | SEQ ID No. 33 | GMRLTLRVYAYSSCCKAS |
| 34 | SEQ ID No. 34 | YVQTKDPVVAALRQRLAT |
| 35 | SEQ ID No. 35 | DVIRYHVSMTSSVNFPD |

TABLE 1-continued

| Sequence ID Numbers and the respective sequences LIST of promiscuous epitopes [peptides] used | | |
|---|---|---|
| 36 | SEQ ID No. 36 | KWVPGYRLVDSTGQVVRTLPAAV |
| 37 | SEQ ID No. 37 | VVNYPPMLLSRDGRDD |
| 38 | SEQ ID No. 38 | MRLSLTALSAGVGAVAMSLTVGA |
| 39 | SEQ ID No. 39 | FNASPVAQSYLRNFLAAPPP |
| 40 | SEQ ID No. 40 | MIIPDINLLLYAVITGFP |
| 41 | SEQ ID No. 41 | LFGFLRIATSARVLAAP |
| 42 | SEQ ID No. 42 | YVREWLSQPNVDLLTAGPRHL |
| 43 | SEQ ID No. 43 | ALGLLDKLGTASHLTT |
| 44 | SEQ ID No. 44 | QYLGSGHAVIVSINAEMIWG |
| 45 | SEQ ID No. 45 | MTTMITLRRRFAVAVAGVA |
| 46 | SEQ ID No. 46 | AYFVVDATKAYCPQYASQL |
| 47 | SEQ ID No. 47 | LALRASAGLVAGMAMAA |
| 48 | SEQ ID No. 48 | PLILVFGRVSELSTCS |
| 49 | SEQ ID No. 49 | LRLVGGVLRVLVVVGAVFDVA |
| 50 | SEQ ID No. 50 | VNIGNALWARLQPCVNW |
| 51 | SEQ ID No. 51 | LVFLAVLVIFAIIVVAKSVALIP |
| 52 | SEQ ID No. 52 | LNIDTVVYFQVTVPQAA |
| 53 | SEQ ID No. 53 | LRVARVELRSIDPPPSIQ |
| 54 | SEQ ID No. 54 | AALQGFTRLLGKPGEDG |
| 55 | SEQ ID No. 55 | YQQITDVVIARGLSQRG |
| 56 | SEQ ID No. 56 | GMTPYLVRVLGTQPTPVQQ |
| 57 | SEQ ID No. 57 | MRVVSTLLSIPLMIGLAVPAHAGP |
| 58 | SEQ ID No. 58 | MITNLRRRTAMAAAGLG |
| 59 | SEQ ID No. 59 | GAALGLGILLVPTVDAHLA |
| 60 | SEQ ID No. 60 | RWFVVWLGTANNPVDKG |
| 61 | SEQ ID No. 61 | GYWVISYPLYGVQQVG |
| 62 | SEQ ID No. 62 | NQLGILNGLLGPTGG |
| 63 | SEQ ID No. 63 | EATATVNAIRGSVTPAVS |
| 64 | SEQ ID No. 64 | VVAYLVNVTVRPGYNF |
| 65 | SEQ ID No. 65 | YQASYLLSQAVNELC |
| 66 | SEQ ID No. 66 | QYGILTGVFHTDIAS |
| 67 | SEQ ID No. 67 | NGFGISLKIGSVDYQMPYQP |
| 68 | SEQ ID No. 68 | VVYQMQPVVFGAPLPLDP |
| 69 | SEQ ID No. 69 | FVNQGGWMLSRASAME |
| 70 | SEQ ID No. 70 | IRVAENVLRSQGIRAWPVC |
| 71 | SEQ ID No. 71 | VRTVPSAVALVTFAGAALS |
| 72 | SEQ ID No. 72 | DLMANIRYMSADPPSMAA |
| 73 | SEQ ID No. 73 | FNADSSKYMITLHTPIAGG |
| 74 | SEQ ID No. 74 | GIVAVAIAVVLMFGLANTPRA |

TABLE 1-continued

| Sequence ID Numbers and the respective sequences LIST of promiscuous epitopes [peptides] used | | |
|---|---|---|
| 75 | SEQ ID No. 75 | FVGIATRADVGAMQSFVSKYNLNF |
| 76 | SEQ ID No. 76 | VFYRADGTSTFVNNPTAAMS |
| 77 | SEQ ID No. 77 | MRSYLLRIELADRPGSLGSLAVALG |
| 78 | SEQ ID No. 78 | LQVLVNEAPRVLRVSWCTVLR |
| 79 | SEQ ID No. 79 | MRYLIATAVLVAVVLVGW |
| 80 | SEQ ID No. 80 | TWYKAFNYNLATSQPITFDTLFVP |
| 81 | SEQ ID No. 81 | IYPIVQRELARQTGF |
| 82 | SEQ ID No. 82 | IFYFAQGELLPSFVGACQAQV |
| 83 | SEQ ID No. 83 | MHRRTALKLPLLLAAGTVLG |
| 84 | SEQ ID No. 84 | LARFHGFNTVRVFLHDLLWAQD |
| 85 | SEQ ID No. 85 | FVAIAARYHIKPLFVLFDSCWD |
| 86 | SEQ ID No. 86 | HPNGRPYRDGEVQTIRKLNGMPS |
| 87 | SEQ ID No. 87 | MRPYYIAIVGSGPSAFFAAAS |
| 88 | SEQ ID No. 88 | RFRFFGNVVVGEHVQPGEL |
| 89 | SEQ ID No. 89 | LESLRPRGIQEVVIVGRRGPLQA |
| 90 | SEQ ID No. 90 | VFRFLTSPIEIKGKRK |
| 91 | SEQ ID No. 91 | LVVRSVGYRGVPTPGLP |
| 92 | SEQ ID No. 92 | WRGSARSYRGTIPKLSLTGL |
| 93 | SEQ ID No. 93 | WLRLVRATSSSRNLMAIM |
| 94 | SEQ ID No. 94 | VLLNAAVRRIDRHGAGV |
| 95 | SEQ ID No. 95 | FVIVAIPPAHRVAIEFDPPLPP |
| 96 | SEQ ID No. 96 | WRAYALPVLMVLTTVVVYQTVTGTS |
| 97 | SEQ ID No. 97 | FVRIDSGKPDFRISLVSPT |
| 98 | SEQ ID No. 98 | YRQYVINHEVGHAIGYL |
| | | Promiscuous CD8 epitopes from *M. tuberculosis* |
| 99 | SEQ ID No. 99 | QIMYNYPAM |
| 100 | SEQ ID No. 100 | IMYNYPAML |
| 101 | SEQ ID No. 101 | AMLGHAGDM |
| 102 | SEQ ID No. 102 | AMEDLVRAY |
| 103 | SEQ ID No. 103 | FVRSSNLKF |

We claim:

1. A synthetic immunogen of general formula 1

$$X_1-Y-X_2$$
$$|$$
$$S$$
$$|$$
$$S$$
$$|$$
$$TLR\ ligand$$

general formula 1 wherein,
- $X_1$ = a promiscuous CD4 T helper epitope having binding ability to HLA class II peptide, said HLA selected from the group consisting of HLA-DR, HLA-DP and HLA-DQ, wherein said CD4 T helper epitope is SEQ ID No. 1;
- $X_2$ = a promiscuous CD8 T cytotoxic epitope having binding ability to HLA class I peptide, said HLA selected from the group consisting of HLA-A, HLA-B and HLA-C, wherein said CD8 T cell epitope is selected from SEQ ID No. 99 to 103;
- Y=Lysine; and
- S=Serine;
  - wherein the promiscuous epitopes represented by SEQ ID No. 1 and SEQ ID NO: 99 to 103 are from *Mycobacterium tuberculosis*.

2. A synthetic immunogen represented by the formula:

$$X_1\cdots Y$$
$$\vdots$$
$$S$$
$$\vdots$$
$$S$$
$$\vdots$$
$$TLR\ ligand$$

wherein $X_1$ = a promiscuous CD4 T helper epitope having binding ability to HLA class II peptide, said HLA selected from the group consisting of HLA-DR, HLA-DP and HLA-DQ, wherein said CD4 T helper epitope is SEQ ID No. 1; and
Y=Lysine; and
S=Serine,
wherein the promiscuous epitopes represented by SEQ ID No. 1 are from *Mycobacterium tuberculosis*.

3. An immunogen as claimed in claim 1, represented by the formula:

$$SEQ\ ID\ NO.\ 1\text{-}Y\text{-}SEQ\ ID\ NO.\ 103$$
$$|$$
$$S$$
$$|$$
$$S$$
$$|$$
$$TLR\ ligand$$

wherein, Y=Lysine and S=Serine.

4. An immunogen as claimed in claim 1, wherein the TLR ligand is selected from the group consisting of TLR1, TLR2, TLR3, TLR4, TLR5, TLR6, TLR7, TLR8, TLR9, TLR10, TLR11, TLR12 and TLR13 ligands; or wherein the TLR ligand is selected from the group consisting of diacyl lipopeptides, triacyl lipopeptides, lipoarabinomanan and lipopolysaccharides.

5. An immunogen as claimed in claim 1, wherein the TLR ligand is S-[2,3-bis(palmitoyloxy)propyl]cysteine.

6. An immunogen as claimed in claim 1, wherein the promiscuous CD4 T helper epitope from *M. tuberculosis* is identified based on T cell proliferation and secretion of IFN-γ and IL-4; or wherein the promiscuous CD4 T helper epitope from *M. tuberculosis* is identified based on the secretion of cytokines IL-2, IL-4, IL-12 and IFN-γ.

7. An immunogen as claimed in claim 1, wherein the promiscuous CD4 T helper epitope from *M. tuberculosis* enhances MHC/HLA expression; or wherein the promiscuous CD4 T helper epitope from *M. tuberculosis* enhances the expression of co-stimulatory molecules selected from CD80, CD86 and CD40.

8. An immunogen as claimed in claim 1, wherein the promiscuous epitopes from *M. tuberculosis* enhance the proliferation of $CD4^+$ and $CD8^+$ T cells by upregulating the expression of CD69 and CD44; or wherein the promiscuous epitopes enhances $CD4^+$ and $CD8^+$ T cell memory, including both central and effector T cell memory.

9. An immunogen as claimed in claim 1, wherein the promiscuous epitopes from *M. tuberculosis* modulate the secretion of cytokines IL-2, IL-4, IL-5, IL-6, IL-10, IL-12, IFN-γ and TNF-α; wherein the promiscuous epitopes modulate the expression of CD44, CD62L and CD127 on memory $CD4^+$ and $CD8^+$ T cells.

10. An immunogen as claimed in claim 1, wherein the promiscuous epitopes from *M. tuberculosis* exploit[s] TLR ligands as adjuvants and hence extra adjuvants are not required.

11. An immunogen as claimed in claim 1, wherein it is coated to/encapsulated in nanoparticles.

12. An immunogen as claimed in claim 1, wherein it is covalently coupled to/entrapped in mannosylated liposomes or liposomes which are tagged with anti-DEC-205 antibody.

13. A pharmaceutical injectable composition comprising the immunogen as claimed in claim 1 with at least one of a pharmaceutically acceptable carrier, diluent and excipient.

14. A method of inducing an immune response against tuberculosis in a subject, comprising administering to the subject a therapeutically effective amount of the immunogen as claimed in claim 1 optionally along with pharmaceutically acceptable carriers, diluents or excipients.

* * * * *

SEQUENCE LISTING

<160> NUMBER OF SEQ ID NOS: 103

<210> SEQ ID NO 1
<211> LENGTH: 20
<212> TYPE: PRT
<213> ORGANISM: Mycobacterium tuberculosis

<400> SEQUENCE: 1

Ser Glu Phe Ala Tyr Gly Ser Phe Val Arg Thr Val Ser Leu Pro Val
1               5                   10                  15

Gly Ala Asp Glu
            20

<210> SEQ ID NO 2
<211> LENGTH: 20
<212> TYPE: PRT
<213> ORGANISM: Mycobacterium tuberculosis

<400> SEQUENCE: 2

Leu Phe Ala Ala Phe Pro Ser Phe Ala Gly Leu Arg Pro Thr Phe Asp
1               5                   10                  15

Thr Arg Leu Met
            20

<210> SEQ ID NO 3
<211> LENGTH: 17
<212> TYPE: PRT
<213> ORGANISM: Mycobacterium tuberculosis

<400> SEQUENCE: 3

Thr Tyr Gly Ile Ala Ser Thr Leu Leu Gly Val Leu Ser Val Ala Ala
1               5                   10                  15

Val

<210> SEQ ID NO 4
<211> LENGTH: 15
<212> TYPE: PRT
<213> ORGANISM: Mycobacterium tuberculosis

<400> SEQUENCE: 4

Val Val Glu Lys Leu Arg Thr His Ser Ser Gly Arg Ile Glu Ala
1               5                   10                  15

<210> SEQ ID NO 5
<211> LENGTH: 15
<212> TYPE: PRT
<213> ORGANISM: Mycobacterium tuberculosis

<400> SEQUENCE: 5

Gln Thr Val His Trp Asn Leu Arg Leu Asp Val Ser Asp Val Asp
1               5                   10                  15

<210> SEQ ID NO 6
<211> LENGTH: 15
<212> TYPE: PRT
<213> ORGANISM: Mycobacterium tuberculosis

<400> SEQUENCE: 6

Leu Leu Ala Val Leu Ile Ala Leu Ala Leu Pro Gly Ala Ala Val
1               5                   10                  15

-continued

```
<210> SEQ ID NO 7
<211> LENGTH: 16
<212> TYPE: PRT
<213> ORGANISM: Mycobacterium tuberculosis

<400> SEQUENCE: 7

Pro Ile Ser Gly Leu Gln Ala Ile Gly Leu Met Gln Ala Val Gln Gly
1               5                   10                  15

<210> SEQ ID NO 8
<211> LENGTH: 17
<212> TYPE: PRT
<213> ORGANISM: Mycobacterium tuberculosis

<400> SEQUENCE: 8

Thr Leu Val Gln Ile Ile Arg Trp Leu Arg Pro Gly Ala Val Ile Ala
1               5                   10                  15

Ile

<210> SEQ ID NO 9
<211> LENGTH: 16
<212> TYPE: PRT
<213> ORGANISM: Mycobacterium tuberculosis

<400> SEQUENCE: 9

Gly Tyr Lys Val Phe Pro Val Leu Asn Leu Ala Val Gly Gly Ser Gly
1               5                   10                  15

<210> SEQ ID NO 10
<211> LENGTH: 16
<212> TYPE: PRT
<213> ORGANISM: Mycobacterium tuberculosis

<400> SEQUENCE: 10

Leu Arg Gln Arg Ile Ser Gln Gln Leu Phe Ser Phe Gly Asp Pro Thr
1               5                   10                  15

<210> SEQ ID NO 11
<211> LENGTH: 18
<212> TYPE: PRT
<213> ORGANISM: Mycobacterium tuberculosis

<400> SEQUENCE: 11

Ile Leu Arg Ala Gly Ala Ala Phe Leu Val Leu Gly Ile Ala Ala Ala
1               5                   10                  15

Thr Phe

<210> SEQ ID NO 12
<211> LENGTH: 15
<212> TYPE: PRT
<213> ORGANISM: Mycobacterium tuberculosis

<400> SEQUENCE: 12

Arg Tyr Met Ile Asp Phe Asn Asn His Ala Asn Leu Gln Gln Ala
1               5                   10                  15

<210> SEQ ID NO 13
<211> LENGTH: 21
<212> TYPE: PRT
<213> ORGANISM: Mycobacterium tuberculosis
```

<400> SEQUENCE: 13

Phe Ala Trp Val Asn His Met Lys Ile Phe Phe Asn Asn Lys Gly Val
1               5                   10                  15

Val Ala Lys Gly Thr
            20

<210> SEQ ID NO 14
<211> LENGTH: 15
<212> TYPE: PRT
<213> ORGANISM: Mycobacterium tuberculosis

<400> SEQUENCE: 14

Gln Trp Gly Ser Leu Pro Ser Leu Arg Val Tyr Pro Ser Gln Val
1               5                   10                  15

<210> SEQ ID NO 15
<211> LENGTH: 25
<212> TYPE: PRT
<213> ORGANISM: Mycobacterium tuberculosis

<400> SEQUENCE: 15

Phe Leu Gln Arg Asn Leu Pro Arg Gly Thr Thr Gly Gln Ala Phe
1               5                   10                  15

Gln Phe Leu Gly Ala Ala Ile Asp His
            20                  25

<210> SEQ ID NO 16
<211> LENGTH: 20
<212> TYPE: PRT
<213> ORGANISM: Mycobacterium tuberculosis

<400> SEQUENCE: 16

Ala Lys Val Val Val Val Gly Gly Leu Val Val Val Leu Ala Val Val
1               5                   10                  15

Ala Ala Ala Ala
            20

<210> SEQ ID NO 17
<211> LENGTH: 15
<212> TYPE: PRT
<213> ORGANISM: Mycobacterium tuberculosis

<400> SEQUENCE: 17

Leu Tyr Arg Lys Leu Thr Thr Thr Thr Val Val Ala Tyr Phe Ser
1               5                   10                  15

<210> SEQ ID NO 18
<211> LENGTH: 15
<212> TYPE: PRT
<213> ORGANISM: Mycobacterium tuberculosis

<400> SEQUENCE: 18

Asp Lys Val Gln Ile Met Gly Val Arg Val Gly Ser Ile Asp Lys
1               5                   10                  15

<210> SEQ ID NO 19
<211> LENGTH: 17
<212> TYPE: PRT
<213> ORGANISM: Mycobacterium tuberculosis

```
<400> SEQUENCE: 19

Val Thr Leu His Tyr Ser Asn Lys Tyr Gln Val Pro Ala Thr Ala Thr
1               5                   10                  15

Ala

<210> SEQ ID NO 20
<211> LENGTH: 15
<212> TYPE: PRT
<213> ORGANISM: Mycobacterium tuberculosis

<400> SEQUENCE: 20

Leu Val Ala Ser Arg Thr Ile Gln Leu Ser Pro Pro Tyr Thr Gly
1               5                   10                  15

<210> SEQ ID NO 21
<211> LENGTH: 15
<212> TYPE: PRT
<213> ORGANISM: Mycobacterium tuberculosis

<400> SEQUENCE: 21

Asp Phe Val Ala Ile Thr Arg Ser Leu Ala Leu Phe Val Ser Ala
1               5                   10                  15

<210> SEQ ID NO 22
<211> LENGTH: 16
<212> TYPE: PRT
<213> ORGANISM: Mycobacterium tuberculosis

<400> SEQUENCE: 22

Thr Ala Leu His Val Leu Pro Thr Tyr Ala Ser Asn Phe Asn Asn Leu
1               5                   10                  15

<210> SEQ ID NO 23
<211> LENGTH: 15
<212> TYPE: PRT
<213> ORGANISM: Mycobacterium tuberculosis

<400> SEQUENCE: 23

Pro Ile Gln Leu Ile Cys Ser Ala Ile Gln Ala Gly Ser Arg Leu
1               5                   10                  15

<210> SEQ ID NO 24
<211> LENGTH: 16
<212> TYPE: PRT
<213> ORGANISM: Mycobacterium tuberculosis

<400> SEQUENCE: 24

Ala Leu Lys Phe Asn Tyr Leu Pro Phe Gly Ser Asn Pro Phe Ser Ser
1               5                   10                  15

<210> SEQ ID NO 25
<211> LENGTH: 16
<212> TYPE: PRT
<213> ORGANISM: Mycobacterium tuberculosis

<400> SEQUENCE: 25

Val Leu Leu Asp Ala Asn Val Leu Ile Ala Leu Val Val Ala Glu His
1               5                   10                  15

<210> SEQ ID NO 26
<211> LENGTH: 17
<212> TYPE: PRT
<213> ORGANISM: Mycobacterium tuberculosis
```

-continued

```
<400> SEQUENCE: 26

Ser Leu Val Arg Phe Leu Val Arg Ser Gly Gln Ser Ala Ala Ala Ala
1               5                   10                  15

Arg

<210> SEQ ID NO 27
<211> LENGTH: 17
<212> TYPE: PRT
<213> ORGANISM: Mycobacterium tuberculosis

<400> SEQUENCE: 27

Met Thr Ala Arg Ser Val Val Leu Ser Val Leu Leu Gly Ala His Pro
1               5                   10                  15

Ala

<210> SEQ ID NO 28
<211> LENGTH: 16
<212> TYPE: PRT
<213> ORGANISM: Mycobacterium tuberculosis

<400> SEQUENCE: 28

Val Arg Ser Ala Asp Gly Tyr Arg Leu Ser Asp Arg Leu Leu Ala Arg
1               5                   10                  15

<210> SEQ ID NO 29
<211> LENGTH: 15
<212> TYPE: PRT
<213> ORGANISM: Mycobacterium tuberculosis

<400> SEQUENCE: 29

Trp His Met Leu Ile Val Thr Ser Ile Gly Thr Asp Ala Arg Thr
1               5                   10                  15

<210> SEQ ID NO 30
<211> LENGTH: 17
<212> TYPE: PRT
<213> ORGANISM: Mycobacterium tuberculosis

<400> SEQUENCE: 30

Phe Val Val Ala Ala Ala Met Val Arg His Leu Leu Thr Asp Pro Met
1               5                   10                  15

Leu

<210> SEQ ID NO 31
<211> LENGTH: 23
<212> TYPE: PRT
<213> ORGANISM: Mycobacterium tuberculosis

<400> SEQUENCE: 31

Met Val Leu Arg Ser Arg Lys Ser Thr Leu Gly Val Val Val Cys Leu
1               5                   10                  15

Ala Leu Val Leu Gly Gly Pro
            20

<210> SEQ ID NO 32
<211> LENGTH: 18
<212> TYPE: PRT
<213> ORGANISM: Mycobacterium tuberculosis
```

-continued

<400> SEQUENCE: 32

Ser Leu Arg Val Ser Trp Arg Gln Leu Gln Pro Thr Asp Pro Arg Thr
1               5                   10                  15

Leu Pro

<210> SEQ ID NO 33
<211> LENGTH: 18
<212> TYPE: PRT
<213> ORGANISM: Mycobacterium tuberculosis

<400> SEQUENCE: 33

Gly Met Arg Leu Thr Leu Arg Val Tyr Ala Tyr Ser Ser Cys Cys Lys
1               5                   10                  15

Ala Ser

<210> SEQ ID NO 34
<211> LENGTH: 18
<212> TYPE: PRT
<213> ORGANISM: Mycobacterium tuberculosis

<400> SEQUENCE: 34

Tyr Val Gln Thr Lys Asp Pro Val Val Ala Ala Leu Arg Gln Arg Leu
1               5                   10                  15

Ala Thr

<210> SEQ ID NO 35
<211> LENGTH: 17
<212> TYPE: PRT
<213> ORGANISM: Mycobacterium tuberculosis

<400> SEQUENCE: 35

Asp Val Ile Arg Tyr His Val Ser Met Thr Ser Ser Val Asn Phe Pro
1               5                   10                  15

Asp

<210> SEQ ID NO 36
<211> LENGTH: 23
<212> TYPE: PRT
<213> ORGANISM: Mycobacterium tuberculosis

<400> SEQUENCE: 36

Lys Trp Val Pro Gly Tyr Arg Leu Val Asp Ser Thr Gly Gln Val Val
1               5                   10                  15

Arg Thr Leu Pro Ala Ala Val
            20

<210> SEQ ID NO 37
<211> LENGTH: 16
<212> TYPE: PRT
<213> ORGANISM: Mycobacterium tuberculosis

<400> SEQUENCE: 37

Val Val Asn Tyr Pro Pro Met Leu Leu Ser Arg Asp Gly Arg Asp Asp
1               5                   10                  15

<210> SEQ ID NO 38
<211> LENGTH: 23
<212> TYPE: PRT
<213> ORGANISM: Mycobacterium tuberculosis

```
<400> SEQUENCE: 38

Met Arg Leu Ser Leu Thr Ala Leu Ser Ala Gly Val Gly Ala Val Ala
1               5                   10                  15

Met Ser Leu Thr Val Gly Ala
            20

<210> SEQ ID NO 39
<211> LENGTH: 20
<212> TYPE: PRT
<213> ORGANISM: Mycobacterium tuberculosis

<400> SEQUENCE: 39

Phe Asn Ala Ser Pro Val Ala Gln Ser Tyr Leu Arg Asn Phe Leu Ala
1               5                   10                  15

Ala Pro Pro Pro
            20

<210> SEQ ID NO 40
<211> LENGTH: 18
<212> TYPE: PRT
<213> ORGANISM: Mycobacterium tuberculosis

<400> SEQUENCE: 40

Met Ile Ile Pro Asp Ile Asn Leu Leu Leu Tyr Ala Val Ile Thr Gly
1               5                   10                  15

Phe Pro

<210> SEQ ID NO 41
<211> LENGTH: 17
<212> TYPE: PRT
<213> ORGANISM: Mycobacterium tuberculosis

<400> SEQUENCE: 41

Leu Phe Gly Phe Leu Arg Ile Ala Thr Ser Ala Arg Val Leu Ala Ala
1               5                   10                  15

Pro

<210> SEQ ID NO 42
<211> LENGTH: 21
<212> TYPE: PRT
<213> ORGANISM: Mycobacterium tuberculosis

<400> SEQUENCE: 42

Tyr Val Arg Glu Trp Leu Ser Gln Pro Asn Val Asp Leu Leu Thr Ala
1               5                   10                  15

Gly Pro Arg His Leu
            20

<210> SEQ ID NO 43
<211> LENGTH: 16
<212> TYPE: PRT
<213> ORGANISM: Mycobacterium tuberculosis

<400> SEQUENCE: 43

Ala Leu Gly Leu Leu Asp Lys Leu Gly Thr Ala Ser His Leu Thr Thr
1               5                   10                  15

<210> SEQ ID NO 44
<211> LENGTH: 20
<212> TYPE: PRT
<213> ORGANISM: Mycobacterium tuberculosis
```

```
<400> SEQUENCE: 44

Gln Tyr Leu Gly Ser Gly His Ala Val Ile Val Ser Ile Asn Ala Glu
1               5                   10                  15

Met Ile Trp Gly
            20

<210> SEQ ID NO 45
<211> LENGTH: 19
<212> TYPE: PRT
<213> ORGANISM: Mycobacterium tuberculosis

<400> SEQUENCE: 45

Met Thr Thr Met Ile Thr Leu Arg Arg Arg Phe Ala Val Ala Val Ala
1               5                   10                  15

Gly Val Ala

<210> SEQ ID NO 46
<211> LENGTH: 19
<212> TYPE: PRT
<213> ORGANISM: Mycobacterium tuberculosis

<400> SEQUENCE: 46

Ala Tyr Phe Val Val Asp Ala Thr Lys Ala Tyr Cys Pro Gln Tyr Ala
1               5                   10                  15

Ser Gln Leu

<210> SEQ ID NO 47
<211> LENGTH: 17
<212> TYPE: PRT
<213> ORGANISM: Mycobacterium tuberculosis

<400> SEQUENCE: 47

Leu Ala Leu Arg Ala Ser Ala Gly Leu Val Ala Gly Met Ala Met Ala
1               5                   10                  15

Ala

<210> SEQ ID NO 48
<211> LENGTH: 16
<212> TYPE: PRT
<213> ORGANISM: Mycobacterium tuberculosis

<400> SEQUENCE: 48

Pro Leu Ile Leu Val Phe Gly Arg Val Ser Glu Leu Ser Thr Cys Ser
1               5                   10                  15

<210> SEQ ID NO 49
<211> LENGTH: 21
<212> TYPE: PRT
<213> ORGANISM: Mycobacterium tuberculosis

<400> SEQUENCE: 49

Leu Arg Leu Val Gly Gly Val Leu Arg Val Leu Val Val Val Gly Ala
1               5                   10                  15

Val Phe Asp Val Ala
            20

<210> SEQ ID NO 50
<211> LENGTH: 17
<212> TYPE: PRT
<213> ORGANISM: Mycobacterium tuberculosis
```

```
<400> SEQUENCE: 50

Val Asn Ile Gly Asn Ala Leu Trp Ala Arg Leu Gln Pro Cys Val Asn
1               5                   10                  15
Trp

<210> SEQ ID NO 51
<211> LENGTH: 23
<212> TYPE: PRT
<213> ORGANISM: Mycobacterium tuberculosis

<400> SEQUENCE: 51

Leu Val Phe Leu Ala Val Leu Val Ile Phe Ala Ile Ile Val Val Ala
1               5                   10                  15
Lys Ser Val Ala Leu Ile Pro
            20

<210> SEQ ID NO 52
<211> LENGTH: 17
<212> TYPE: PRT
<213> ORGANISM: Mycobacterium tuberculosis

<400> SEQUENCE: 52

Leu Asn Ile Asp Thr Val Val Tyr Phe Gln Val Thr Val Pro Gln Ala
1               5                   10                  15
Ala

<210> SEQ ID NO 53
<211> LENGTH: 18
<212> TYPE: PRT
<213> ORGANISM: Mycobacterium tuberculosis

<400> SEQUENCE: 53

Leu Arg Val Ala Arg Val Glu Leu Arg Ser Ile Asp Pro Pro Pro Ser
1               5                   10                  15
Ile Gln

<210> SEQ ID NO 54
<211> LENGTH: 17
<212> TYPE: PRT
<213> ORGANISM: Mycobacterium tuberculosis

<400> SEQUENCE: 54

Ala Ala Leu Gln Gly Phe Thr Arg Leu Leu Gly Lys Pro Gly Glu Asp
1               5                   10                  15
Gly

<210> SEQ ID NO 55
<211> LENGTH: 17
<212> TYPE: PRT
<213> ORGANISM: Mycobacterium tuberculosis

<400> SEQUENCE: 55

Tyr Gln Gln Ile Thr Asp Val Val Ile Ala Arg Gly Leu Ser Gln Arg
1               5                   10                  15
Gly

<210> SEQ ID NO 56
<211> LENGTH: 19
<212> TYPE: PRT
<213> ORGANISM: Mycobacterium tuberculosis
```

```
<400> SEQUENCE: 56

Gly Met Thr Pro Tyr Leu Val Arg Val Leu Gly Thr Gln Pro Thr Pro
1               5                   10                  15

Val Gln Gln

<210> SEQ ID NO 57
<211> LENGTH: 24
<212> TYPE: PRT
<213> ORGANISM: Mycobacterium tuberculosis

<400> SEQUENCE: 57

Met Arg Val Val Ser Thr Leu Leu Ser Ile Pro Leu Met Ile Gly Leu
1               5                   10                  15

Ala Val Pro Ala His Ala Gly Pro
            20

<210> SEQ ID NO 58
<211> LENGTH: 17
<212> TYPE: PRT
<213> ORGANISM: Mycobacterium tuberculosis

<400> SEQUENCE: 58

Met Ile Thr Asn Leu Arg Arg Arg Thr Ala Met Ala Ala Ala Gly Leu
1               5                   10                  15

Gly

<210> SEQ ID NO 59
<211> LENGTH: 19
<212> TYPE: PRT
<213> ORGANISM: Mycobacterium tuberculosis

<400> SEQUENCE: 59

Gly Ala Ala Leu Gly Leu Gly Ile Leu Leu Val Pro Thr Val Asp Ala
1               5                   10                  15

His Leu Ala

<210> SEQ ID NO 60
<211> LENGTH: 17
<212> TYPE: PRT
<213> ORGANISM: Mycobacterium tuberculosis

<400> SEQUENCE: 60

Arg Trp Phe Val Val Trp Leu Gly Thr Ala Asn Asn Pro Val Asp Lys
1               5                   10                  15

Gly

<210> SEQ ID NO 61
<211> LENGTH: 16
<212> TYPE: PRT
<213> ORGANISM: Mycobacterium tuberculosis

<400> SEQUENCE: 61

Gly Tyr Trp Val Ile Ser Tyr Pro Leu Tyr Gly Val Gln Gln Val Gly
1               5                   10                  15

<210> SEQ ID NO 62
<211> LENGTH: 15
<212> TYPE: PRT
<213> ORGANISM: Mycobacterium tuberculosis
```

```
<400> SEQUENCE: 62

Asn Gln Leu Gly Ile Leu Asn Gly Leu Leu Gly Pro Thr Gly Gly
1               5                   10                  15

<210> SEQ ID NO 63
<211> LENGTH: 18
<212> TYPE: PRT
<213> ORGANISM: Mycobacterium tuberculosis

<400> SEQUENCE: 63

Glu Ala Thr Ala Thr Val Asn Ala Ile Arg Gly Ser Val Thr Pro Ala
1               5                   10                  15

Val Ser

<210> SEQ ID NO 64
<211> LENGTH: 16
<212> TYPE: PRT
<213> ORGANISM: Mycobacterium tuberculosis

<400> SEQUENCE: 64

Val Val Ala Tyr Leu Val Asn Val Thr Val Arg Pro Gly Tyr Asn Phe
1               5                   10                  15

<210> SEQ ID NO 65
<211> LENGTH: 15
<212> TYPE: PRT
<213> ORGANISM: Mycobacterium tuberculosis

<400> SEQUENCE: 65

Tyr Gln Ala Ser Tyr Leu Leu Ser Gln Ala Val Asn Glu Leu Cys
1               5                   10                  15

<210> SEQ ID NO 66
<211> LENGTH: 15
<212> TYPE: PRT
<213> ORGANISM: Mycobacterium tuberculosis

<400> SEQUENCE: 66

Gln Tyr Gly Ile Leu Thr Gly Val Phe His Thr Asp Ile Ala Ser
1               5                   10                  15

<210> SEQ ID NO 67
<211> LENGTH: 20
<212> TYPE: PRT
<213> ORGANISM: Mycobacterium tuberculosis

<400> SEQUENCE: 67

Asn Gly Phe Gly Ile Ser Leu Lys Ile Gly Ser Val Asp Tyr Gln Met
1               5                   10                  15

Pro Tyr Gln Pro
            20

<210> SEQ ID NO 68
<211> LENGTH: 18
<212> TYPE: PRT
<213> ORGANISM: Mycobacterium tuberculosis

<400> SEQUENCE: 68

Val Val Tyr Gln Met Gln Pro Val Val Phe Gly Ala Pro Leu Pro Leu
1               5                   10                  15

Asp Pro
```

-continued

```
<210> SEQ ID NO 69
<211> LENGTH: 16
<212> TYPE: PRT
<213> ORGANISM: Mycobacterium tuberculosis

<400> SEQUENCE: 69

Phe Val Asn Gln Gly Gly Trp Met Leu Ser Arg Ala Ser Ala Met Glu
1               5                   10                  15

<210> SEQ ID NO 70
<211> LENGTH: 19
<212> TYPE: PRT
<213> ORGANISM: Mycobacterium tuberculosis

<400> SEQUENCE: 70

Ile Arg Val Ala Glu Asn Val Leu Arg Ser Gln Gly Ile Arg Ala Trp
1               5                   10                  15

Pro Val Cys

<210> SEQ ID NO 71
<211> LENGTH: 19
<212> TYPE: PRT
<213> ORGANISM: Mycobacterium tuberculosis

<400> SEQUENCE: 71

Val Arg Thr Val Pro Ser Ala Val Ala Leu Val Thr Phe Ala Gly Ala
1               5                   10                  15

Ala Leu Ser

<210> SEQ ID NO 72
<211> LENGTH: 18
<212> TYPE: PRT
<213> ORGANISM: Mycobacterium tuberculosis

<400> SEQUENCE: 72

Asp Leu Met Ala Asn Ile Arg Tyr Met Ser Ala Asp Pro Pro Ser Met
1               5                   10                  15

Ala Ala

<210> SEQ ID NO 73
<211> LENGTH: 19
<212> TYPE: PRT
<213> ORGANISM: Mycobacterium tuberculosis

<400> SEQUENCE: 73

Phe Asn Ala Asp Ser Ser Lys Tyr Met Ile Thr Leu His Thr Pro Ile
1               5                   10                  15

Ala Gly Gly

<210> SEQ ID NO 74
<211> LENGTH: 21
<212> TYPE: PRT
<213> ORGANISM: Mycobacterium tuberculosis

<400> SEQUENCE: 74

Gly Ile Val Ala Val Ala Ile Ala Val Val Leu Met Phe Gly Leu Ala
1               5                   10                  15

Asn Thr Pro Arg Ala
            20
```

<210> SEQ ID NO 75
<211> LENGTH: 24
<212> TYPE: PRT
<213> ORGANISM: Mycobacterium tuberculosis

<400> SEQUENCE: 75

Phe Val Gly Ile Ala Thr Arg Ala Asp Val Gly Ala Met Gln Ser Phe
1               5                   10                  15

Val Ser Lys Tyr Asn Leu Asn Phe
            20

<210> SEQ ID NO 76
<211> LENGTH: 20
<212> TYPE: PRT
<213> ORGANISM: Mycobacterium tuberculosis

<400> SEQUENCE: 76

Val Phe Tyr Arg Ala Asp Gly Thr Ser Thr Phe Val Asn Asn Pro Thr
1               5                   10                  15

Ala Ala Met Ser
            20

<210> SEQ ID NO 77
<211> LENGTH: 25
<212> TYPE: PRT
<213> ORGANISM: Mycobacterium tuberculosis

<400> SEQUENCE: 77

Met Arg Ser Tyr Leu Leu Arg Ile Glu Leu Ala Asp Arg Pro Gly Ser
1               5                   10                  15

Leu Gly Ser Leu Ala Val Ala Leu Gly
            20                  25

<210> SEQ ID NO 78
<211> LENGTH: 21
<212> TYPE: PRT
<213> ORGANISM: Mycobacterium tuberculosis

<400> SEQUENCE: 78

Leu Gln Val Leu Val Asn Glu Ala Pro Arg Val Leu Arg Val Ser Trp
1               5                   10                  15

Cys Thr Val Leu Arg
            20

<210> SEQ ID NO 79
<211> LENGTH: 18
<212> TYPE: PRT
<213> ORGANISM: Mycobacterium tuberculosis

<400> SEQUENCE: 79

Met Arg Tyr Leu Ile Ala Thr Ala Val Leu Val Ala Val Val Leu Val
1               5                   10                  15

Gly Trp

<210> SEQ ID NO 80
<211> LENGTH: 24
<212> TYPE: PRT
<213> ORGANISM: Mycobacterium tuberculosis

```
<400> SEQUENCE: 80

Thr Trp Tyr Lys Ala Phe Asn Tyr Asn Leu Ala Thr Ser Gln Pro Ile
1               5                   10                  15

Thr Phe Asp Thr Leu Phe Val Pro
            20

<210> SEQ ID NO 81
<211> LENGTH: 15
<212> TYPE: PRT
<213> ORGANISM: Mycobacterium tuberculosis

<400> SEQUENCE: 81

Ile Tyr Pro Ile Val Gln Arg Glu Leu Ala Arg Gln Thr Gly Phe
1               5                   10                  15

<210> SEQ ID NO 82
<211> LENGTH: 21
<212> TYPE: PRT
<213> ORGANISM: Mycobacterium tuberculosis

<400> SEQUENCE: 82

Ile Phe Tyr Phe Ala Gln Gly Glu Leu Leu Pro Ser Phe Val Gly Ala
1               5                   10                  15

Cys Gln Ala Gln Val
            20

<210> SEQ ID NO 83
<211> LENGTH: 20
<212> TYPE: PRT
<213> ORGANISM: Mycobacterium tuberculosis

<400> SEQUENCE: 83

Met His Arg Arg Thr Ala Leu Lys Leu Pro Leu Leu Leu Ala Ala Gly
1               5                   10                  15

Thr Val Leu Gly
            20

<210> SEQ ID NO 84
<211> LENGTH: 22
<212> TYPE: PRT
<213> ORGANISM: Mycobacterium tuberculosis

<400> SEQUENCE: 84

Leu Ala Arg Phe His Gly Phe Asn Thr Val Arg Val Phe Leu His Asp
1               5                   10                  15

Leu Leu Trp Ala Gln Asp
            20

<210> SEQ ID NO 85
<211> LENGTH: 22
<212> TYPE: PRT
<213> ORGANISM: Mycobacterium tuberculosis

<400> SEQUENCE: 85

Phe Val Ala Ile Ala Ala Arg Tyr His Ile Lys Pro Leu Phe Val Leu
1               5                   10                  15

Phe Asp Ser Cys Trp Asp
            20
```

-continued

<210> SEQ ID NO 86
<211> LENGTH: 23
<212> TYPE: PRT
<213> ORGANISM: Mycobacterium tuberculosis

<400> SEQUENCE: 86

His Pro Asn Gly Arg Pro Tyr Arg Asp Gly Glu Val Gln Thr Ile Arg
1 5 10 15

Lys Leu Asn Gly Met Pro Ser
20

<210> SEQ ID NO 87
<211> LENGTH: 21
<212> TYPE: PRT
<213> ORGANISM: Mycobacterium tuberculosis

<400> SEQUENCE: 87

Met Arg Pro Tyr Tyr Ile Ala Ile Val Gly Ser Gly Pro Ser Ala Phe
1 5 10 15

Phe Ala Ala Ala Ser
20

<210> SEQ ID NO 88
<211> LENGTH: 19
<212> TYPE: PRT
<213> ORGANISM: Mycobacterium tuberculosis

<400> SEQUENCE: 88

Arg Phe Arg Phe Phe Gly Asn Val Val Val Gly Glu His Val Gln Pro
1 5 10 15

Gly Glu Leu

<210> SEQ ID NO 89
<211> LENGTH: 23
<212> TYPE: PRT
<213> ORGANISM: Mycobacterium tuberculosis

<400> SEQUENCE: 89

Leu Glu Ser Leu Arg Pro Arg Gly Ile Gln Glu Val Val Ile Val Gly
1 5 10 15

Arg Arg Gly Pro Leu Gln Ala
20

<210> SEQ ID NO 90
<211> LENGTH: 16
<212> TYPE: PRT
<213> ORGANISM: Mycobacterium tuberculosis

<400> SEQUENCE: 90

Val Phe Arg Phe Leu Thr Ser Pro Ile Glu Ile Lys Gly Lys Arg Lys
1 5 10 15

<210> SEQ ID NO 91
<211> LENGTH: 17
<212> TYPE: PRT
<213> ORGANISM: Mycobacterium tuberculosis

<400> SEQUENCE: 91

Leu Val Val Arg Ser Val Gly Tyr Arg Gly Val Pro Thr Pro Gly Leu
1 5 10 15

Pro

<210> SEQ ID NO 92
<211> LENGTH: 20
<212> TYPE: PRT
<213> ORGANISM: Mycobacterium tuberculosis

<400> SEQUENCE: 92

Trp Arg Gly Ser Ala Arg Ser Tyr Arg Gly Thr Ile Pro Lys Leu Ser
1 5 10 15

Leu Thr Gly Leu
20

<210> SEQ ID NO 93
<211> LENGTH: 18
<212> TYPE: PRT
<213> ORGANISM: Mycobacterium tuberculosis

<400> SEQUENCE: 93

Trp Leu Arg Leu Val Arg Ala Thr Ser Ser Ser Arg Asn Leu Met Ala
1 5 10 15

Ile Met

<210> SEQ ID NO 94
<211> LENGTH: 17
<212> TYPE: PRT
<213> ORGANISM: Mycobacterium tuberculosis

<400> SEQUENCE: 94

Val Leu Leu Asn Ala Ala Val Arg Arg Ile Asp Arg His Gly Ala Gly
1 5 10 15

Val

<210> SEQ ID NO 95
<211> LENGTH: 22
<212> TYPE: PRT
<213> ORGANISM: Mycobacterium tuberculosis

<400> SEQUENCE: 95

Phe Val Ile Val Ala Ile Pro Pro Ala His Arg Val Ala Ile Glu Phe
1 5 10 15

Asp Pro Pro Leu Pro Pro
20

<210> SEQ ID NO 96
<211> LENGTH: 25
<212> TYPE: PRT
<213> ORGANISM: Mycobacterium tuberculosis

<400> SEQUENCE: 96

Trp Arg Ala Tyr Ala Leu Pro Val Leu Met Val Leu Thr Thr Val Val
1 5 10 15

Val Tyr Gln Thr Val Thr Gly Thr Ser
20 25

<210> SEQ ID NO 97
<211> LENGTH: 19
<212> TYPE: PRT
<213> ORGANISM: Mycobacterium tuberculosis

<400> SEQUENCE: 97

Phe Val Arg Ile Asp Ser Gly Lys Pro Asp Phe Arg Ile Ser Leu Val
1 5 10 15

Ser Pro Thr

```
<210> SEQ ID NO 98
<211> LENGTH: 17
<212> TYPE: PRT
<213> ORGANISM: Mycobacterium tuberculosis

<400> SEQUENCE: 98

Tyr Arg Gln Tyr Val Ile Asn His Glu Val Gly His Ala Ile Gly Tyr
1               5                  10                  15

Leu

<210> SEQ ID NO 99
<211> LENGTH: 9
<212> TYPE: PRT
<213> ORGANISM: Mycobacterium tuberculosis

<400> SEQUENCE: 99

Gln Ile Met Tyr Asn Tyr Pro Ala Met
1               5

<210> SEQ ID NO 100
<211> LENGTH: 9
<212> TYPE: PRT
<213> ORGANISM: Mycobacterium tuberculosis

<400> SEQUENCE: 100

Ile Met Tyr Asn Tyr Pro Ala Met Leu
1               5

<210> SEQ ID NO 101
<211> LENGTH: 9
<212> TYPE: PRT
<213> ORGANISM: Mycobacterium tuberculosis

<400> SEQUENCE: 101

Ala Met Leu Gly His Ala Gly Asp Met
1               5

<210> SEQ ID NO 102
<211> LENGTH: 9
<212> TYPE: PRT
<213> ORGANISM: Mycobacterium tuberculosis

<400> SEQUENCE: 102

Ala Met Glu Asp Leu Val Arg Ala Tyr
1               5

<210> SEQ ID NO 103
<211> LENGTH: 9
<212> TYPE: PRT
<213> ORGANISM: Mycobacterium tuberculosis

<400> SEQUENCE: 103

Phe Val Arg Ser Ser Asn Leu Lys Phe
1               5
```